United States Patent [19]
Herzinger

[11] Patent Number: 5,835,222
[45] Date of Patent: Nov. 10, 1998

[54] SYSTEM, AND MATHEMATICAL REGRESSION-BASED METHOD UTILIZING OPTICAL DATA, FOR IDENTIFYING OPTICAL AXIS ORIENTATION IN MATERIAL SYSTEMS SUCH AS OPTICAL COMPENSATORS AND RETARDERS

[75] Inventor: Craig M. Herzinger, Lincoln, Nebr.

[73] Assignee: J.A. Woollam Co. Inc., Lincoln, Nebr.

[21] Appl. No.: 910,594

[22] Filed: Jul. 31, 1997

Related U.S. Application Data

[63] Continuation-in-part of Ser. No. 515,738, Aug. 16, 1995, abandoned, which is a continuation-in-part of Ser. No. 422,346, Apr. 14, 1995, Pat. No. 5,757,494.

[51] Int. Cl.⁶ .................................................. G01N 21/21
[52] U.S. Cl. .......................... 356/369; 356/365; 356/367; 250/225
[58] Field of Search .................................. 356/364–369; 250/225

[56] References Cited

U.S. PATENT DOCUMENTS

| | | | |
|---|---|---|---|
| 3,741,661 | 6/1973 | Yamamoto et al. | 356/117 |
| 3,880,524 | 4/1975 | Dill et al. | 356/118 |
| 4,053,232 | 10/1977 | Dill et al. | 356/118 |
| 4,176,951 | 12/1979 | Robert et al. | 356/33 |
| 5,181,080 | 1/1993 | Fanton et al. | 356/381 |
| 5,311,285 | 5/1994 | Oshige et al. | 356/369 |
| 5,329,357 | 7/1994 | Bernoux et al. | 356/369 |
| 5,335,066 | 8/1994 | Yamada et al. | 356/364 |
| 5,373,359 | 12/1994 | Woollam et al. | 356/328 |
| 5,416,588 | 5/1995 | Ducharme et al. | 356/369 |
| 5,504,583 | 4/1996 | Johs et al. | 356/369 |
| 5,521,706 | 5/1996 | Green et al. | 356/369 |
| 5,581,350 | 12/1996 | Chen et al. | 356/369 |
| 5,757,494 | 5/1998 | Green et al. | 356/369 |

OTHER PUBLICATIONS

Regression calibration method for rotating element ellipsometers, Johs, Thin Solid Films, 234, 1993.
Data analysis for spectroscopic ellipsometry, Jellison Jr., Thin Solid Films, 234 1993.
Oriel Data Sheets for quartz & mica retarder.
Meadowlark Optics Data Sheets for Zero–Order Retarders.
Meadowlark Optics Data Sheet for Achromatic Retarder.
New Focus Data Sheet Titled "The Berek Polarization Compensator".
Berek Retarder Equation Sheet for Ideal Berek Retarder, provided by New Focus.
Excerpts from PH.D. Thesis of Mathias Schubert at Leipzig University in 1996.

*Primary Examiner*—Hoa O. Pham
*Attorney, Agent, or Firm*—James D. Welch

[57] ABSTRACT

Disclosed is a system, and regression-based method utilizing optical data, for use in identifying material systems which have been cut to have an optical axis oriented as desired with respect to a alignment surface. The present invention is particularly well suited to qualification of material systems such as optical compensators and retarders, which ideally have an optical axis oriented perpendicular to, or parallel to, an alignment surface.

17 Claims, 7 Drawing Sheets

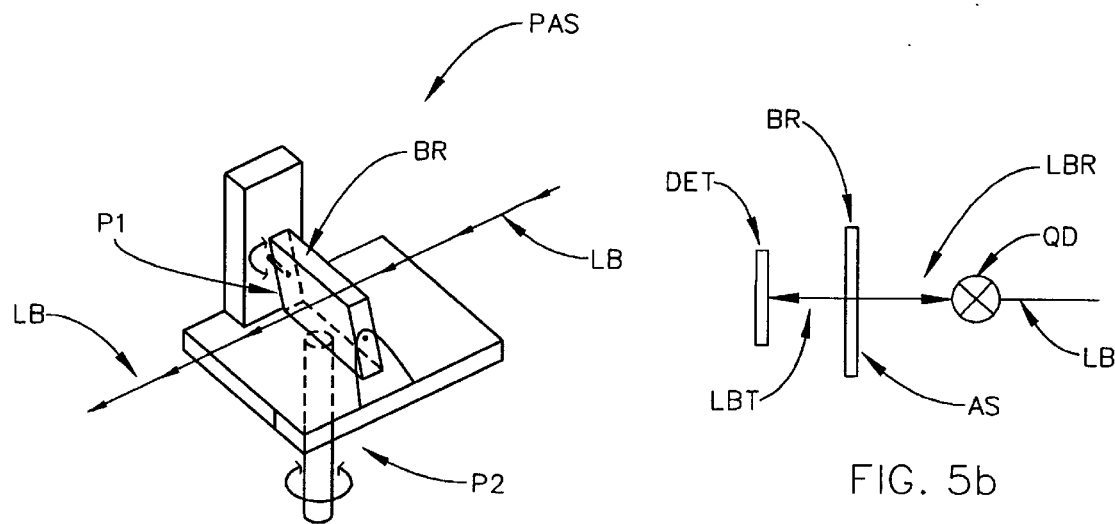
FIG. 5a
FIG. 5b
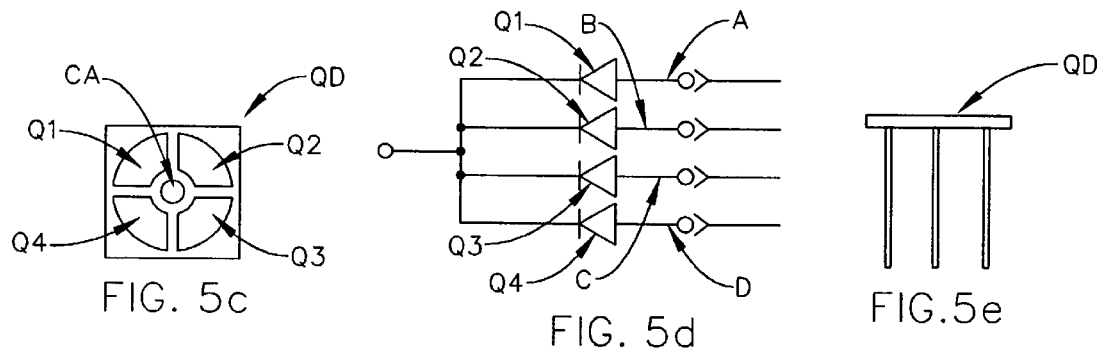
FIG. 5c
FIG. 5d
FIG. 5e
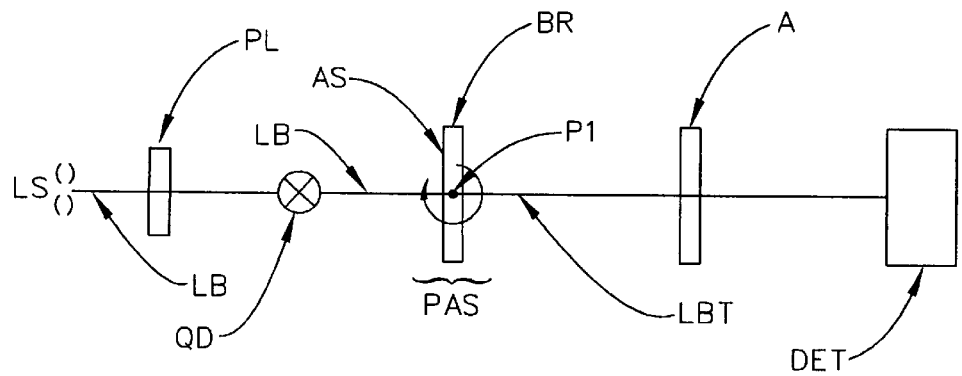
FIG. 6a

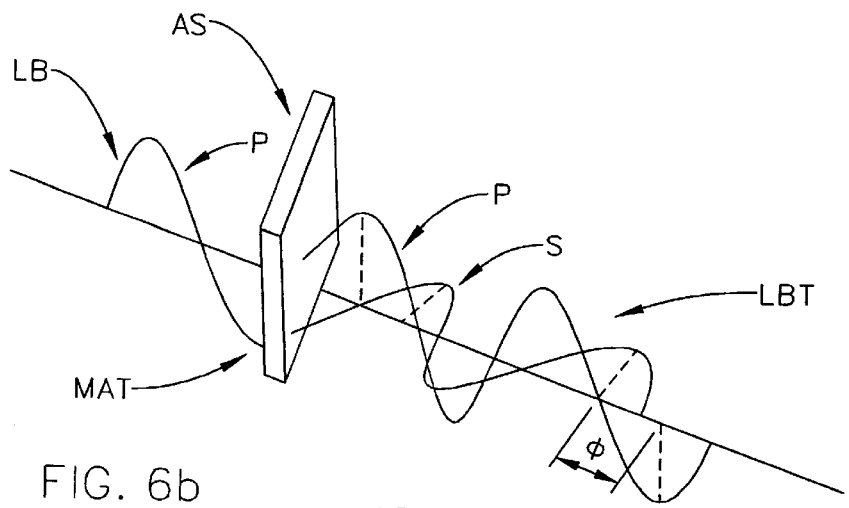
FIG. 6b
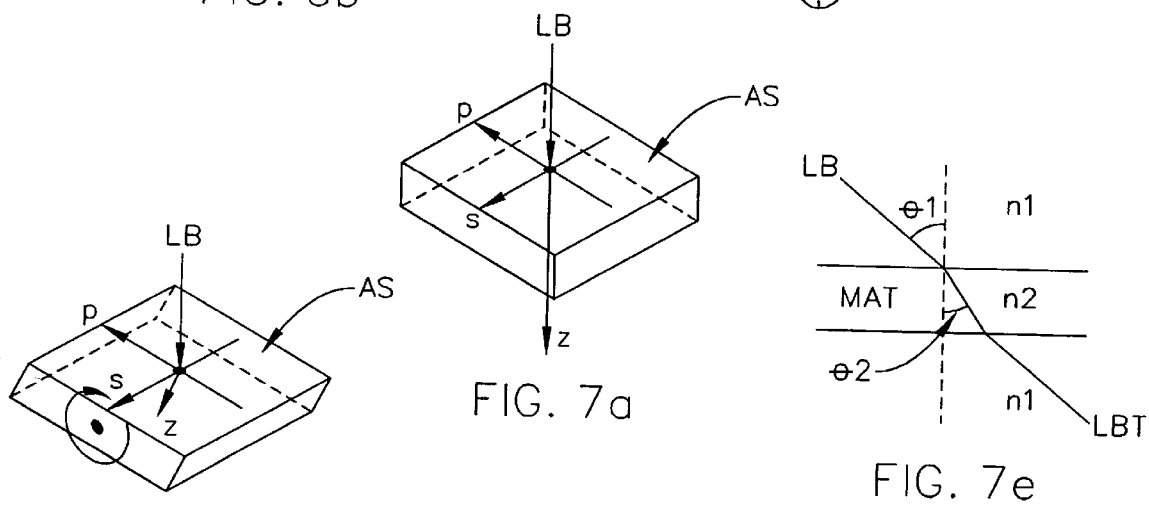
FIG. 7a
FIG. 7b
FIG. 7e
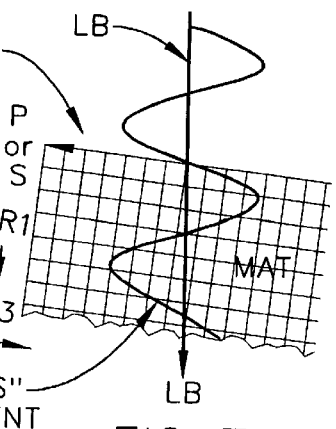
FIG. 7c
FIG. 7d

SYSTEM, AND MATHEMATICAL REGRESSION-BASED METHOD UTILIZING OPTICAL DATA, FOR IDENTIFYING OPTICAL AXIS ORIENTATION IN MATERIAL SYSTEMS SUCH AS OPTICAL COMPENSATORS AND RETARDERS

This application is a Continuation-In-Part of patent application Ser. No. 08/515,738, filed Aug. 16, 1995 (abandoned), which is a Continuation-In-Part of patent application Ser. No. 08/422,346, filed Apr. 14, 1995 (now U.S. Pat. No. 5,757,494).

TECHNICAL FIELD

The present invention relates to material systems such as optical compensators and retarders, and more particularly is a system, and regression-based method utilizing optical data, for qualifying a material system as having an optical axis oriented as desired with respect to an alignment surface thereof.

BACKGROUND

Ellipsometry is a well known method of monitoring a change in polarization state in a beam of electromagnetic radiation as a result of interaction with a material system. In general a beam of electromagnetic radiation is conditioned to present with a known polarization state, (eg. linear), then is caused to interact with, (ie. reflect from or be transmitted through), a material system, and then is detected and analyzed to determine the resulting state of polarization thereof. The change in polarization state caused by interaction with a material system is determinative of numerical values for material system characterizing parameters.

To provide necessary insight, it must be understood that a polarized beam of electromagnetic radiation can be considered to be comprised of two related orthogonal components. In the context of an ellipsometer with a material system present therein, said related orthogonal components can be identified as a "P" component, which is oriented in a plane including said incident electromagnetic beam and a perpendicular to said material system surface, and an "S" component which is oriented perpendicular to said "P" orthogonal component and simultaneously parallel to the surface of said material system surface. It is also noted that what ellipsometers measure is a ratio of magnitudes of "P" and "S" components and a phase angle between said "P" and "S" components. This can be represented as:

$$rho = tp/ts = \tan(PSI) \cdot \exp(i \cdot DELTA),$$

where tp and ts are complex amplitudes which can be measured in a beam of electromagnetic radiation transmitted through a material system, and (PSI) and (DELTA) are characterizing angles associated with a material system.

It is also necessary to understand that a Jones Matrix representation can be utilized to describe the effect that interaction with a material system has on a beam of polarized electromagnetic radiation. For instance, where an input-polarized beam of electromagnetic radiation is caused to impinge upon and be transmitted through a material system which is characterized by "P" and "S" components of magnitudes Epi and Esi respectively, multiplication by an appropriately evaluated sample system representing Jones Matrix, allows calculation of magnitudes of output "P" and "S" components Epo and Eso. This can be mathematically represented as:

$$\begin{bmatrix} Epo \\ Eso \end{bmatrix} = \begin{bmatrix} Tpp & Tsp \\ Tps & Tpp \end{bmatrix} \times \begin{bmatrix} Epi \\ Esi \end{bmatrix}$$

Continuing, the use of optical compensators/retarders, which serve to introduce phase delay between related orthogonal components, (such as "S" and "P" components of a polarized electromagnetic beam which interacts therewith), in for instance, ellipsometer, polarimeter and reflectometer systems, is well known.

It is also well known that optical compensators/retarders have associated therewith a an "optical axis" which is typically oriented essentially parallel to, or essentially perpendicular to, an alignment surface thereof. Optical compensators/retarders which have an optical axis oriented essentially parallel to an alignment surface are commonly applied in ellipsometer systems, and allow control of retardation effected between orthogonal components in an electromagnetic beam caused to pass therethrough via rotation thereof about an axis perpendicular to said alignment surface. Optical compensators/retarders with an optical axis oriented essentially perpendicular to an alignment surface have been less commonly applied in ellipsometer systems, and are known as "Berek-type". It is noted that Berek-type compensators/retarders allow control of retardation effected between orthogonal components in an electromagnetic beam caused to pass therethrough via a "tilting" of an "alignment surface", rather than a "rotation" thereof. An advantage of a Berek-type compensator/retarder is that it can effect continuous "tilt-effected" retardation over a relatively large range which does not have an inherent three-hundred-sixty (360) degree rotation repeat cycle.

While the optical axis of a material system, such as a crystalline material optical compensator/retarder provided by a typical manufacturing procedure, can generally be expected to be very nearly parallel to, or perpendicular to, an alignment surface, (as provided by a supplier), in practice it occurs that an optical axis identified as "parallel" or "perpendicular" to an alignment, (ie. reference), surface thereof will have associated therewith some error in said orientation. In most instances this can be tolerated as negligible. However, there are instances where the optical axis of a retarder/compensator utilized in a ellipsometer system must be essentially "ideal". For instance, a preferred embodiment of recent invention by the J. A. Woollam Co. Inc., requires, for optimum results, use of a Berek-type retarder/compensator which is known to have an optical axis oriented perpendicular to an alignment surface of said retarder/compensator, to within a very tight tolerance range, (eg. within hundredths of a degree). Said invention comprises positioning a Berek-type compensator/retarder in a rotating element, or modulator element containing ellipsometer system for the purpose of imposing an intended amount of retardation between orthogonal components, (eg. "P" and "S"), in an electromagnetic beam utilized to investigate a material system, so an effective DELTA of said sample system is placed into a range in which it can be accurately measured. In combination with, for instance, the adjustment of a Polarizer, (which controls the magnitude of the ratio of orthogonal, such as "P" and "S", components), it is possible to condition the polarization state, (eg. magnitude of the ratio of orthogonal components and the phase angle therebetween), of a material system investigating electromagnetic beam in an ellipsometer system, such that a material system which presents with a PSI and/or DELTA which is not directly measurable by an ellipsometer system, can be investigated. (The Berek-type retarder/compensator can alternatively be viewed as forming "composite material system" with the material system per se. being investigated, said "composite material system" being characterized by a DELTA which the ellipsometer can measure with acceptable accuracy). Data obtained then must only be subjected to appropriate direct transfer function or indirect mathematical regression procedure(s) which serves to compensate the effect of setting said Berek-type retarder/compensator and/ or Polarizer, for instance, to arrive at material system per se. PSI and DELTA values. For instance, said approach allows utilizing Rotating Analyzer and Rotating Polarizer ellipsometers to investigate material systems per se. with DELTA's near zero (0.0) and one-hundred-eighty (180) degrees, and utilizing Modulation Element ellipsometers to investigate material systems with PSI's near forty-five (45) degrees, said identified DELTA and PSI values being typically unmeasurable by the identified ellipsometer systems.

As alluded to, while perhaps not always required, in certain circumstances it is necessary to identify how the optical axis in a material system is oriented with respect to an alignment surface thereof. A known approach to this is by use of known "X-ray Crystallography" techniques. While "X-ray Crystallography" techniques unquestionably identify a crystal axis, the practice thereof requires specialized and expensive equipment which is not available in many laboratories in which ellipsometry is practiced. As well, to identify an optical axis by "X-Ray Crystallography" techniques, one must assume that an identified crystal axis coincides with an optical axis. This is not always the case as demonstrated by polycrystaline materials which present a predominate optical axis direction, and by materials which are utilized in magneto-optics.

A reference which serves to describe ellipsometry and polarized light generally, and which is incorporated by reference herein, is that by Azzam and Bashara titled, "Ellipsometry and Polarized Light", published by North-Holland in 1989.

A Search for relevant Patents and other References conducted with respect to copending patent application Ser. No. 08/515,738, (which is a Continuation-In-Part of pending patent application Ser. No. 08/422,346 from which Applications the present Application is a Continuation-In-Part), which identified Applications describe systems and/or methods which might benefit from utility provided by the present invention, produced very little. Identified Patents were: U.S. Pat. No. 3,741,661 to Yamamoto et al.; U.S. Pat. No. 4,176,951 to Robert et al.; U.S. Pat. No. 5,181,080 to Fanton et al.; U.S. Pat. No. 5,311,285 to Oshige; U.S. Pat. No. 5,335,066 to Yamada et al. Also U.S. Pat. No. 4,053,232 to Dill et al; and U.S. Pat. No. 5,329,357 to Bernoux et al. were identified. None of said Patents are considered to be particularly relevant. Patents which describe ellipsometers which the present invention can benefit are, for instance, U.S. Pat. No. 5,373,359 to Woollam et al., and U.S. Pat. No. 5,416,588 to Ducharme et al., which Patents apply to Rotating Analyzer and Modulator Ellipsometers respectively, were also identified. Also identified for a similar reason are Patents to Green et al. and Johs et al., U.S. Pat. Nos. 5,521,706 and 5,504,582 respectively. Another identified Patent, to Dill et al., U.S. Pat. No. 3,880,524, describes the use of a quarter-waveplate Compensator between a Polarizer and a Rotating Analyzer in a Rotating Analyzer Ellipsometer (RAE), such that the state of polarization of a reflected beam of light from a Sample System can be varied arbitrarily by merely adjusting the angular position (azimuths) of the Polarizer and said quarter-waveplate Compensator. Said quarter-waveplate Compensator can be placed ahead or after a Sample System. The system described in Dill et al. provides a means for adjusting both ellipsometric ALPHA and ellipsometric BETA in a polarized beam of light, which polarized beam is "monochromatic". The above referenced book by Azzam and Bashara briefly mentions the use of a Variable Retarder, (Babinet-Soleil type), to control relative retardation of Orthogonal Components in a polarized Light Beam in Nulling Ellipsometers, but discourages such use because of associated poor resolution capability, (see page 166, footnote 9). In addition, as the present invention utilizes regression to evaluate parameters in a mathematical model, a book titled "Numerical Recipes in C", Cambridge University Press, 1988 is incorporated by reference. Also disclosed is an Article by Johs, titled "Regression Calibration Method For Rotating Element Ellipsometers, Thin Solid Films, 234 (1993). This article describes a regressions approach to calibration of rotating element ellipsometers, and is relevant to the present invention, as the present invention, in part, utilizes a mathematical regression procedure, and is incorporated herein by reference. A Patent which describes the use of Regression in an ellipsometer is U.S. Pat. No. 5,581,350 to Chen et al. Another article, which is also incorporated herein by reference, titled "Data Analysis for Spectroscopic Ellipsometry", by Jellison Jr., Thin Solid Films, 234, (1993) p. 416–422, is identified as it describes a method of determining the accuracy with which certain data points, (for instance, ALPHA or BETA values), can be measured, which information allows adding a weighting factor to a curve fitting regression procedure as applied to a multiplicity of said data, which weighting factor serves to emphasize the effect of more accurate and precise data.

In addition, a PH.D. Thesis titled "Generalized Ellipsometry and Complex Optical Systems Spontaneously Ordered AlInP and GaInP", by Mathias Schubert, which was presented to Leipzig University in 1996 is identified and incorporate by reference hereinto, (including references cited therein), for the purpose of providing insight to practical Mathematical Modeling of Retarder/Compensator Systems in numerical computing systems. While the following Disclosure provides insight to Mathematical Modeling of Retarder/Compensator Systems meant to provide intuitive insight, the interested reader might wish to access the Schubert Thesis for a demonstration of Mathematics utilized in a computer aided "number crunching" setting.

In view of the foregoing, it should be readily appreciated that a system and method utilizing optical data, (such as that readily obtainable from use of an ellipsometer system), which serves to identify optical compensators/retarders which present with an optical axis oriented as desired, with respect to an alignment surface thereof, would provide utility. There is thus identified a need, and the present invention serves to meet said need.

DISCLOSURE OF THE INVENTION

The present invention is a method for investigating material systems which have one or more optical axis, such as uni-axial and bi-axial materials, said material systems being typically, but not necessarily, crystalline. The present invention can be applied to aide original manufacture and in after market quality control settings and involves use of ellipsometric optical means to identify the direction of an optical axis with respect to an "alignment surface" of said material system. An important example of application of the present invention is in qualifying optical retarders/compensators as having an optical axis oriented as desired with respect to an alignment surface thereof. Typically an "ideal" optical retarder/compensator will have an optical axis oriented in a locus precisely perpendicular to or precisely parallel to an alignment surface thereof, thus, in particular, the present invention is very well suited to identifying material systems, selected from a lot thereof, as meeting the criteria of having an optical axis which is oriented sufficiently perpendicular to, or to material systems which have an optical axis oriented sufficiently parallel to an alignment surface thereof, as to be considered "ideal", in a practical application sense.

To understand the present invention it is important to first understand that a crystalline material system, for instance, which is cut into a cubic shape, has associated therewith three (3) indices of refraction. Ideally two (2) of said indices of refraction can be observed as orthogonally oriented with respect to one another in a surface of said crystalline material system, and the third (3rd) index of refraction can be considered to, ideally, project perpendicularly with respect to the first two indices of refraction, into the bulk of said cube shaped material system. As well, said ideal cube of crystalline material can be considered to have an optical axis which is oriented precisely perpendicular to, or precisely parallel to said surface, (termed an alignment surface herein), in which are present said two (2) observable orthogonally oriented indices of refraction. If an ideally cut cube of crystalline material were available and a polarized beam of electromagnetic radiation, which presents with both "P" and "S" components, (described supra herein), were caused to impinge upon said alignment surface of said cube of crystalline material along a perpendicular to said surface, then two indices of refraction would generally be presented to said polarized beam of electromagnetic radiation, (ie. one refractive index for the "P" and one refractive index for the "S" component), by said cube of crystalline material. If such a polarized beam of electromagnetic radiation is caused to pass through such an ideal cube of crystalline material, the "P" and "S" components of said polarized beam of electromagnetic radiation will be subjected to different indices of refraction and a change in polarization state will occur in said polarized beam of electromagnetic radiation, and said polarization state change will comprise a phase angle retardation between said "P" and "S" components which depends on the "difference" in the refractive indices encountered by each of said "P" and "S" components. It is noted that if, as can occur in ideal crystalline material with an optical axis directed precisely perpendicular to a surface thereof, (ie. a Berek-type optical retarder/compensator), the two indices of refraction "seen" by "P" and "S" components of a polarized beam of electromagnetic radiation are equal, there will of course be no relative retardation difference entered between said "P" and "S" components by passage of said polarized beam of electromagnetic radiation through said cube of crystalline material.

Now, while an ideal cube of crystalline material can be considered to have an optical axis which is precisely perpendicular to, or precisely parallel to an alignment surface thereof as described, such that the direction of an optical axis can be directly identified by observation of the orientation of a surface, (an alignment surface), of said cube of crystalline material, a cube of crystalline material can be cut such that an optical axis is oriented other than precisely perpendicular or precisely parallel to a surface thereof. Such could result from manufacturing tolerance introduced error, for instance. The presence of such "unknown" manufacturing tolerance introduced error in coincident alignment of an optical axis with a direction parallel or perpendicular to an alignment surface, can make precision usage of such a cube of crystalline material difficult, because simple alignment of a beam of electromagnetic radiation so that it impinges upon a surface of said non-ideal cube of crystalline material along a locus perpendicular to the plane of said surface, will "see", and be subject to, modification by more than two (2) "known" indices of refraction as it passes through said cube of non-perfect crystalline material. That is, a third index of refraction can be "seen" by and effect the "P" and/or "S" component and cause a total retardation between said "P" and "S" components which can not be explained by the presence of only two (2) expected to be "seen" indices of refraction. This same effect can be observed when a crystalline material with an optical axis oriented perpendicular to an alignment surface is physically "tilted" with respect to an incident polarized beam of electromagnetic radiation, to place the locus of said incident beam of electromagnetic radiation other than coincident with the optical axis, and in fact the effect is useful in practical settings. While involvement of a third index of refraction in causing different effective refractive indices to be "seen" by "P" and "S" components in a polarized beam of electromagnetic radiation is thus not in itself detrimental, (and can be utilized with benefit), if its effect is not provided for in analysis of data influenced thereby, (because of an unjustified assumption of an ideal optical axis orientation with respect to an alignment surface in a crystalline material), said analysis will obviously not yield accurate results.

As an example, the Background Section herein identified a usage of a Berek-type retarder/compensator in an ellipsometer wherein it is important to know that an optical axis of said Berek-type retarder/compensator is oriented in a locus essentially coincident with, (within hundredths of a degree), a direction perpendicular to an alignment surface thereof. (Note that Berek-type retarders/compensators can be considered to be a "Plate" of crystalline material such as would be achieved by reducing a dimension in a direction along an optical axis of the cube of crystalline material described infra herein). Continuing, while it is relatively easy to align a beam of electromagnetic radiation so that it impinges upon an alignment surface of a Berek-type retarder/compensator along a locus which is perpendicular to said alignment surface, (see the Detailed Description Section of this Disclosure which describes use of a Quadrature Detector to said end), it generally requires "X-ray Crystalography" analysis to directly identify the orientation of an optical axis in a crystalline material which has been cut to provide an identifiable alignment surface.

The problem which the present invention addresses is thus exemplified by the fact that Berek-type retarders/compensators obtained from manufacturers differ in degrees of "ideality" regarding coincidence of a perpendicular to an alignment surface and an optical axis thereof, and in some application precise knowledge of how much an optical axis deviates from a perpendicular to an alignment surface in a Berek-type retarder/compensator, is required to allow productive use thereof. The present invention allows use of ellipsometric optical means, (rather than "X-ray Crystalography" means which can be relatively less accessible to many researchers), to identify the direction of an optical axis with respect to a crystalline material alignment surface.

Practice of the present invention method allows a user to identify, for instance, specific optical retarders/compensators in lots thereof, which optical retarders/compensators comprise cut crystalline material with an easily identifiable surface thereon which can be utilized as an alignment surface, which crystalline material has an optical axis aligned as desired with respect to said easily identified alignment surface. If an optical axis in a specific optical retarder/compensator is found, by the relatively easy practice of the present invention, to be aligned other than as desired by a user, (eg. not perpendicular or parallel with an alignment surface thereof), said specific optical retarder/compensator can be relatively quickly rejected before use thereof in an ellipsometer or other system causes, for instance, difficult to explain irregularities in data acquired from said system which includes said optical retarder/compensator.

Continuing, it must also be understood that ellipsometry comprises a technique by which a beam of electromagnetic radiation in a known state of polarization is caused to interact with a sample material system, which interaction causes a change in polarization state of said beam of polarized electromagnetic radiation. The change in polarization state is related to properties of the sample material system. What ellipsometry systems measure is a polarization state, (ie. a magnitude of a ratio of orthogonal components, (eg. "P" and "S"), in a polarized beam of electromagnetic radiation, and a phase angle between said orthogonal components). This effectively means that a measured magnitude of said ratio of orthogonal components is generally complex and can be represented as a sum of "real" and "imaginary" parts.

It must further be understood that a material system representing transmission Jones Matrix is a two (2) by two (2) component representation which contains sample material system modeling information, thereby allowing calculation of (output) orthogonal magnitudes (Epo, Eso), of a polarized beam of electromagnetic radiation after interaction thereof with a material system, given the magnitudes (Epi, Esi) of (input) orthogonal magnitudes of a polarized beam of electromagnetic radiation incident upon said material system, prior to said interaction with said material system. A material system representing transmission Jones Matrix relating Epo to Epi and Esi as well as Eso to Epi and Esi is:

$$\begin{bmatrix} Epo \\ Eso \end{bmatrix} = \begin{bmatrix} Tpp & Tsp \\ Tps & Tss \end{bmatrix} \times \begin{bmatrix} Epi \\ Esi \end{bmatrix}$$

where Tpp, Tss, Tps and Tsp are the components of the two dimensional material system representing transmission Jones matrix.

Thus, if the magnitudes of orthogonal components of an incident beam of electromagnetic radiation are known, and the material system representing transmission Jones Matrix of a sample material system is known, one can calculate the magnitudes of the orthogonal components of a portion of said incident beam of electromagnetic radiation which is transmitted through, and exits said sample material system.

It is also noted that the practice of ellipsometry generally involves obtaining numerous "data sets" which comprise experimentally determined polarization states, (ie. magnitudes of ratios of orthogonal components and an associated phase angle therebetween), as a function of the angle of incidence at which a beam of electromagnetic radiation is caused to impinge upon an alignment surface of a crystalline material and/or as a function of the wavelength of electromagnetic radiation utilized.

It is further to be understood that while typical practice in ellipsometry provides, (via a regression onto measured data mediated procedure), a ratio which is much like a Jones Matrix on-diagonal ratio:

on-diagonal ratio Tpp/Tss, it is possible to align an ellipsometer system to provide data which allows regression mediated determination of off-diagonal ratios:

off-diagonal ratio Tps/Tpp;
off-diagonal ratio Tsp/Tss;
off-diagonal ratio Tps/Tss;
off-diagonal ratio Tsp/Tpp.

Measurement of off-diagonal ratio(s) can be effected by providing an incident beam of electromagnetic radiation which is linearly polarized and oriented such that it contains only a "P" or "S" component. This can be done at various Angles-of-Incidence of said polarized electromagnetic beam with respect to an alignment surface of said sample material system. If interaction with a material system, (eg. a crystalline material cut to form an optical retarder/compensator with an optical axis oriented parallel or perpendicular to an alignment surface thereof), produces only "P" or "S" polarized electromagnetic beam, respectively, after said interaction, then off-diagonal ratios will have values of zero (0.0), (ie. the sample material system is isotropic). If, however, interaction with a sample material system causes transformation of some "P" component content to "S" component content, or vice-versa, then certain off-diagonal ratios can provide non-zero (0.0) values, at least at some Angles-of-Incidence of said polarized electromagnetic beam with respect to said alignment surface, (ie. the sample material system is anisotropic). It is to be understood then that on-diagonal Jones Matrix components Tpp and Tss serve to describe conversion of "P" ("S") orthogonal components of an incident beam of electromagnetic radiation to corresponding "P" ("S") components, respectively, in an exiting beam of electromagnetic radiation by interaction with a sample material system, while off-diagonal Jones Matrix components Tsp and Tps serve to describe conversion of "P" ("S") orthogonal components in an incident beam of electromagnetic radiation to "S" ("P") components, respectively, in an exiting beam of electromagnetic radiation by interaction with a sample material system. (Note that herein while both isotropic and anisotropic material systems are considered to alter the polarization state of a polarized electromagnetic beam caused to pass therethrough as evidenced in a change in a magnitude of a ratio of orthogonal components and a phase angle delay effected therebetween, the effect of an anisotropic material system on a polarized beam of electromagnetic radiation is not properly described as the result separate changes in orthogonal component ratio magnitude and a phase angle therebetween, because polarized electromagnetic beam "P" components are changed to "S" components (and vice versa) by interaction with an anisotropic material system. As a result, where an anisotropic material system is utilized, it is technically appropriate to speak of a change in a "total polarization state change", rather than a change in the "magnitude of a ratio of orthogonal components" and a separate change in a "phase angle therebetween". It is to be understood, however, that a polarization state change generally, as an end result, includes a change in phase angle between orthogonal components of a polarized electromagnetic beam which has been caused to pass through an anisotropic material system, just as is the case in an isotropic material system is present. Herein mention of an ellipsometrically measurable change in phase angle effected in a polarized beam of electromagnetic radiation by causing it to pass through a material system will be utilized to aid with disclosure, but the reader should keep in mind that where the material system is anisotropic, the change in magnitude of a ratio of orthogonal components, and a change in phase angle therebetween in a beam of polarized electromagnetic radiation caused to pass therethrough, are actually inter-related in a complex manner).

Continuing, by obtaining at least four (4) data sets, (note that if three (3) ratios of Jones matrix components are to be evaluated, only three (3) data sets can suffice), of the magnitude of a ratio of orthogonal components of an electromagnetic beam which has been caused to be transmitted through a crystalline material as a function of angle-of-incidence of an electromagnetic beam to an alignment surface of a sample material system, said data sets being distinguished by the setting of different input electromagnetic beam polarization states for each, it is possible to, typically by a regression procedure, determine values for the components (Tpp, Tsp, Tss, Tps) of a material system representing Jones matrix. It is again noted that at each angle of incidence of said polarized electromagnetic beam with respect to an alignment surface of a sample material system, a ratio of magnitudes of orthogonal components will have associated therewith a phase angle between said orthogonal components which can be measured, hence, ratio(s) of magnitudes orthogonal components of and electromagnetic beam can be expressed as a sum of distinct "real" and "imaginary" parts.

It is noted that evaluation of on-diagonal and off-diagonal ratios of material system representing transmission Jones Matrix components is not new, and it is also noted that discussion thereof is found in references such as that by Azzam and Bashara, which was cited in the Background Section herein, and which is incorporated herein by reference.

Continuing, material systems are generally modeled by physical and optical parameters, such as indices of refraction, differences in indices of refraction, and thickness. The J. A. Woollam Co. Inc. WVASE (Registered Trademark) Program for instance, allows a user to propose a model for a material system, which model includes as variables, parameters selected from the group consisting of (refractive indices, differences in refractive indices and thickness). By regression onto experimentally obtained ellipsometric data accumulated by investigation of said material system utilizing a polarized beam of electromagnetic radiation, reduced-square-error "most-likely" numerical values can be assigned to said sample system characterizing parameters. Most importantly with respect to practice of the present invention, it is possible for ellipsometers to measure polarization states which are determinative of (differences in refractive indices) encountered by "P" and "S" components a beam of electromagnetic radiation by interaction with a material system, and said (differences in refractive indices) can be found with accuracy much greater than can be an index of refraction per se. The measurement of a (differences in refractive indices) is mediated by ellipsometric measurement of a "phase angle retardation" entered between orthogonal components of a polarized beam of electromagnetic radiation, said "phase angle" being the result of said orthogonal components "seeing" different effective refractive indices as they are caused to travel therethrough. (Again, while the "phase angle" is discussed separately, it is to be understood that it is actually just a part of an ellipsometrically determinable Polarization State comprised of a magnitude of a ratio of orthogonal components and said "phase angle" which generally provides an ellipse when said magnitude of said ratio is plotted as a function of said phase angle). Now, while an index of refraction per se. can typically be determined to approximately four (4) to five (5) decimal places by typical ellipsometry techniques, a difference in refractive indices which "P" and "S" components in a beam of polarized electromagnetic radiation "see" as they are caused to be transmitted through a material system which is on the order of one (1) to two (2) Mils thick, can be measured to eight (8) or nine (9) decimal places by ellipsometric measurement of a phase state comprised of a phase angle delay effected between orthogonal components by transmission through said material system. The reason this is possible is that a typically investigated retarder/compensator which is on the order of two (2) mils thick, can represent a large number of wavelengths of a beam of polarized electromagnetic radiation caused to be transmitted therethrough. It is to be understood that each cycle of said beam of polarized electromagnetic radiation, as it is caused to be transmitted through such a retarder/compensator, has imposed thereon a phase delay between orthogonal components thereof, based upon a "difference" in indices of refraction "seen" by the orthogonal components. The summed total phase delay effect between orthogonal components exiting such a retarder/compensator can be on the order of one-tenth ($1/10$) a degree, which is easily measured by ellipsometry as part of a polarization state, and by division, the contribution to the total phase angle delay, on a per cycle basis can be assigned. Again, the phase angle delay difference on a per cycle basis is directly related to the difference in refractive indices "seen" by the orthogonal components. While an ellipsometer measures change in Polarization State effected in an incident beam of polarized electromagnetic radiation caused by passage through a material system, it is to be appreciated that said change in Polarization State determines a measurable "phase angle delay", when the material system is on the order of two (2) mils thick.

A major enabling aspect of the present invention then comprises the ability of ellipsometers to accurately measure such a Polarization State "phase angle" change between associated orthogonal components in a polarized beam of electromagnetic radiation which is caused to be transmitted through a material system, which ability is utilized by the present invention to allow mathematical (regression) based determination of materials system representing transmission Jones matrix components. And in conjunction with performing regression of a derived mathematical model of a material system, (comprising a relationship between indices of refraction, thickness and optical axis direction), onto magnitude values of real and/or imaginary component parts of on-diagonal and/or off-diagonal Jones Matrix ratios, (over a range of at least one member of the group consisting of: (wavelength and "P" plane angles-of-incidence of an investigating polarized beam of electromagnetic radiation to an alignment surface of said material system and in the case of a material system with an optical axis oriented radially therein, perhaps, optical axis radial direction rotation angle), it is the teaching of the present invention that it is possible to determine the orientation of an optical axis with respect to an alignment surface of a material system in orthogonal planes to within hundredths ($1/100$) of a degree. The present invention has effectively added variables identifying "optical axis orientation with respect to an alignment surface of a material system" to those which can be evaluated by the J. A. Woollam Co. WVASE (Registered Trademark) program. It is believed that Patentability is provided by the just described, ratios of material system representing Jones matrix components mediated, regression procedure evaluation of optical axis orientation, aspects of the present invention.

It is further noted that the J. S. Woollam Co. Inc. WVASE (Registered Trademark) program allows fixing a variable, (eg. material system thickness), at a certain value if the value thereof is known. This can reduce the amount of data necessary to allow evaluation of an optical axis orientation with respect to an alignment surface of a crystalline material. This is noted to provide insight to the fact that regression based procedures can vary in the amount of data utilized, and in the number of material system mathematical model parameters evaluated. It is also noted that while there must be sufficient data present, (such as demonstrated by the requirement of three equations to evaluate three unknowns), regression techniques typically provide data sufficient to over-determine parameters to be evaluated thereby. The extra data is utilized to provide error-bars, (ie. confidence levels), around regression procedure provided parameter values. It is often then not possible to specifically identify exactly how much data should be obtained to evaluate parameters by a regression based technique, beyond that minimally required. For instance, if a magnitude of a ratio of Jones Matrix components over a range of angles-of-incidence of a beam of electromagnetic radiation with respect to an alignment surface of a materials system, and/or wavelength, is regressed onto, one might utilize the only "real" part thereof, only the "imaginary" part thereof, or both said "real" and "imaginary" parts. All three approaches can provide an answer. Generally, the use of greater amounts of data will improve accuracy of regression provided results. (It should be understood that real and imaginary parts of a ratio of Jones Matrix components can be thought of as provided by, respectively, effectively multiplying by applying COS and SIN functions of the phase angle between the components of said ratio at a corresponding value of independent variable).

Now, in the case of an ideal Berek-type retarder/compensator, where an optical axis is aligned essentially coincident with a perpendicular to an alignment surface thereof, the indices of refraction "seen" by the "P" and "S" components of an incident polarized beam of electromagnetic radiation caused to impinge upon said alignment surface along a locus coincident with said perpendicular to said alignment surface, are ideally equal. As a result no relative retardation is entered between said "P" and "S" components when said polarized beam of electromagnetic radiation is caused to transverse said "ideal" Berek-type retarder/compensator. (Note that this feature allows physically orienting, (rather than removing), a Berek-type retarder/compensator in an ellipsometer system so that it appears as if it is not present, but for a minor, typically negligible attenuation effect). However, where an optical axis in a Berek-type retarder/compensator is not aligned coincident with a perpendicular to an alignment surface thereof, a polarized beam of electromagnetic radiation caused to impinge upon said crystalline material along a locus which is perpendicular to said alignment surface will be subject to influence by other than two equal value refractive indices, and relative phase angle retardation will be effected between said "P" and "S" components thereof as said polarized beam of electromagnetic radiation is caused to travel through said Berek-type retarder/compensator. It is emphasized that, (assuming there are no effects caused by stress etc. in a Berek-type retarder/compensator), said difference in refractive indices effectively "seen" by said "P" and "S" components of said polarized electromagnetic is directly dependent upon deviation of orientation of the optical axis of an investigated Berek-type retarder/compensator from a perpendicular to said reference surface in "P" and "S" planes when said polarized beam of electromagnetic radiation is caused to impinge upon the alignment surface of said Berek-type retarder/compensator along a locus perpendicular to said alignment surface.

Continuing, even if an optical axis of a Berek-type retarder/compensator is oriented at an angle other than perpendicular to an alignment surface, an appropriate physical orientation of said Berek-type retarder/compensator during investigation utilizing ellipsometric techniques can still cause the Berek-type retarder/compensator to effectively present only a single value for two indices of refraction "seen" by "P" and "S" components of an impinging polarized beam of electromagnetic radiation. For instance, one can visualize a Berek-type retarder/compensator as a plate of crystalline material with an optical axis displaced form an ideal coincidence with respect to a perpendicular to an alignment surface thereof by some angle. If said Berek-type retarder/compensator is then investigated by obtaining ellipsometric data at a plurality of "P" plane "tilt" angles of said Berek-type retarder/compensator, it should be appreciated that at some physical positioning, (effected by rotation about an axis perpendicular to said alignment surface), of said Berek-type retarder/compensator the optical axis which is directed other than coincident with a perpendicular to said alignment surface, will lie completely in the "P" orthogonal component plane during all such "P" plane "tilting". (See Background Section for a description of "P" and "S" planes). That is, for any angle of "P" plane "tilt" of said described Berek-type retarder/compensator, about an appropriate rotation axis, the optical axis will be in the "P" plane. However, and importantly, a symmetry in certain experimentally based ellipsometric data, (magnitude of on-diagonal ratio of Jones Matrix components (Tpp/Tss) obtained at "P" plane "tilts" of said Berek-type retarder/compensator in both clockwise and counter-clockwise about said perpendicular to said alignment surface will not be centered about a perpendicular to said alignment surface. The symmetry in said ellipsometric on-diagonal Jones Matrix components (Tpp/Tss) data will, however, be centered around the optical axis of the Berek-type retarder/compensator in the "P" plane. Thus a shift in an ellipsometric data symmetry point in the "P" plane, (when said Berek-type retarder/compensator is rotated to place the optical axis thereof in the "P" plane throughout "P" plane "tilting"), on an incident beam of electromagnetic radiation, provides data which is directly dependent upon a deviation of said optical axis from coincidence with a perpendicular to said alignment surface. This effect can be visually observed by plotting measured magnitudes of an on-diagonal ratio (Tpp/Tss) with respect to "P" plane "tilt" angles, both clockwise and counterclockwise to said optical axis, when the optical axis is positioned in the "P" plane. Said visual observation alone can aide with practice of the present invention.

Continuing, it should be appreciated that an appropriate ninety (90) degree rotation of said plate of Berek-type retarder/compensator, (about said axis perpendicular to said alignment surface), found oriented as just described, will direct the optical axis thereof toward the "S" direction of the incident beam of electromagnetic radiation. With the Berek-type retarder/compensator in this rotated position, for any "tilt" of said Berek-type retarder/compensator in the "P" plane, (ie. "tilts" of said Berek-type retarder/compensator about the same "tilt" rotational axis as utilized when the plate of crystalline material was rotated about the axis perpendicular to said alignment surface to place the optical axis in the "P" plane throughout all "tilts"), "P" and "S" components of an impinging beam of electromagnetic radiation will, at many said "tilt" angles, "see" different effective indices of refraction which result from contributions from three indices of refraction. The effect of said difference in effective refractive indices seen by said "P" and "S" components of an impinging beam of electromagnetic radiation finds observable expression in the form of non-zero (0.0) magnitudes at at least some "P" plane "tilt" angles in plot(s) of magnitudes of off-diagonal ratios of Jones Matrix components, ((Tsp/Tss), (Tsp/Tpp), (Tps/Tss) and (Tps/Tpp)), with respect to "P" plane angle-of-incidence "tilts" of said polarized beam of electromagnetic radiation.

It is noted that in practice of the present invention method non-ideal Berek-type retarders/compensators are generally positioned so as to present with an optical axis which simultaneously deviates from coincidence with a perpendicular to an alignment surface in both "P" and "S" directions. When this is the case it is still found that plotting the "real" or "imaginary" part of an on-diagonal ratio (Tpp/Tss) as a function of "P" plane "tilt" angle effected angle-of-incidence of said polarized beam of electromagnetic radiation, serves to visually indicate a point of data symmetry and thus identify "P" plane optical axis deviation form coincidence with a perpendicular to said alignment surface, and that plotting of "real" or "imaginary" parts of an off-diagonal ratio as a function of the same "P" plane "tilt" angle effected angle-of-incidence of said polarized beam of electromagnetic radiation, will simultaneously provide non-zero (0.0) results at at least some of said "P" plane Angles-of-Tilt. Said plots demonstrate "P" and "S" direction projections of an optical axis direction, and the present invention regression based procedure allows obtaining numerical values for angular deviations of said optical axis from an ideal direction perpendicular to said alignment surface.

It must be understood that practice of the present invention generally does not typically involve rotation of an investigated non-ideal Berek-type retarder/compensator so that its optical axis is oriented in only a "P" or "S" direction, but rather provides for obtaining sufficient ellipsometric data to allow a regression procedure to determine deviation of an optical axis away from coincidence with a perpendicular to an alignment surface in both "P" and "S" directions. However, in all cases said optical axis deviation away from coincidence with a perpendicular to an alignment surface, in both "P" and "S" directions, is at least in part determined by relative retardation effected between "P" and "S" components of a polarized beam of electromagnetic radiation caused to pass through said Berek-type retarder/compensator, and said relative retardation is caused by a "difference in indices of refraction" seen by "P" and "S" components of said polarized beam of electromagnetic radiation. (In the Berek-type retarder/compensator case the "P" and "S" direction deviation angles are separated by appropriate regression onto diagonal and off-diagonal ratios of Jones Matrix components).

The above discussion is also generally applicable to non-Berek-type retarder/compensator plates of crystalline material which ideally do not have an optical axis oriented perpendicular to an alignment surface thereof. As alluded to above, a Berek-type retarder/compensator plate of crystalline material can be considered to result from a cube of crystalline material when a dimension thereof in the direction of the optical axis is caused to be reduced, however, it is also possible to reduce a dimension of a cube of crystalline material in a direction perpendicular to the direction of an optical axis, and produce a non-Berek-type retarder/compensator. That is, the optical axis of a non-Berek-type retarder/compensator is ideally oriented parallel to an alignment surface thereof, rather than perpendicular thereto. Examples of crystalline materials cut to provide such a result are optical retarders/compensators which effect change in retardation effected between related orthogonal "P" and "S" components in a beam of electromagnetic radiation caused to pass therethrough, by a "rotation" around a rotation axis located centrally in said alignment surface. This is in contrast to the Berek-type retarders/compensators described above which effect change in retardation between orthogonal "P" and "S" components in a beam of electromagnetic radiation caused to pass therethrough, by a "tilt" about a rotation axis oriented parallel to the alignment surface and perpendicular to a reduced dimension surface dimension in a plate of crystalline material which is not utilized as an alignment surface. (It is acknowledged that such a "tilt" is actually just a "rotation", but it is around a rotation axis directed perpendicular to a reduced surface in a plate of crystalline material). It is important to note that the optical axis in such a non-Berek-type retarder/compensator can be other than ideally oriented in such a cut crystalline material by being directed other than along a radial projection from said central located axis of rotation, (usually not a concern), or by being other than parallel to a major surface thereof, (which is of more concern and which is accurately detectable by practice of the present invention). That is, the present invention allows accurate evaluation of an angle of deviation from parallel orientation to an alignment surface of an optical axis in a non-Berek-type retarder/compensator, however, data as a function of two parameters must typically be obtained to evaluate an angle of deviation from parallel to an alignment surface. Parameters in addition to angle of incidence of a beam of polarized electromagnetic radiation with respect to an alignment surface of a material system are wavelength and optical axis radial direction rotation angles, (the later being effected by rotation of a non-Berek-type retarder/compensator about an axis oriented perpendicular to an alignment surface). It is noted that wavelength is the preferred additional parameter in ellipsometer settings, and that typically three (3) angles of incidence of a beam of polarized electromagnetic radiation with respect to an alignment surface of a non-Berek-type retarder/compensator material system, in combination with a multiplicity of second parameter values, are sufficient. This is to be compared to the case of a Berek-type retarder/compensator where a multiplicity of angles of incidence of a beam of polarized electromagnetic radiation with respect to an alignment surface are utilized and only a single second parameter value, (eg. one wavelength), are typically utilized.

To provide further insight it is noted that optical retarders/compensators which effect change in retardation effected between orthogonal components of a beam of electromagnetic radiation caused to pass therethrough by rotation about a centrally oriented axis which is oriented perpendicular to an alignment surface, are typically cut to provide a circularly shaped non-reduced surface area. As well, one can visualize that Berek-type and non-Berek-type retarders/compensators differ only in orientation of their optical axis with respect to an alignment with a non-reduced dimension alignment surface thereof, and said orientation of optical axis with respect to said alignment surface is the effect only of how a crystalline material is cut. That is, the same cube of crystalline material can be cut to provide an optical retarder/compensator with an optical axis perpendicular to or parallel to an alignment surface thereof, and similar errors can occur in cutting both Berek-type and non-Berek-type optical retarders/compensators. Errors in cutting Berek-type optical retarders/compensators are identified by an optical axis thereof being oriented other than perpendicular to an alignment surface, and errors in cutting non-Berek-type optical retarders/compensators are identified by an optical axis thereof being oriented other than parallel to an alignment surface. The present invention allows determination of non-ideal orientation of an optical axis in both Berek-type and non-Berek-type optical retarders/compensators.

Continuing, while the present invention is applicable to determining the angular direction of a radially oriented optical axis in an alignment surface of a non-Berek-type retarder/compensator, and deviation of said optical axis from said orientation parallel to an alignment surface thereof, the method of application is by necessity a bit different, and inherently more difficult, than that required for investigation of Berek-type retarders/compensators. This is because in non-Berek-type retarders/compensators it is generally not known at which angular direction a radial optical axis projects when it first is placed into an ellipsometer for investigation. With Berek-type retarder/compensators it is generally known that the optical axis is projected close to perpendicular with respect to an alignment surface, but with non-Berek-type retarders/compensators knowledge that an optical axis is projected radially, essentially parallel to an alignment surface, still leaves unknown at what angle between zero (0.0) and three-hundred-sixty (360) degrees said radially oriented optical axis projects within said alignment surface. As well, it is not as easy to describe what occurs in a non-Berek-type retarder/compensator as it is not possible to easily separate out, into "P" and "S" components, the effects of "shifted data symmetry in on-diagonal Jones Matrix (Tpp/Tss) ratio as a function of "tilt" angle in a "P" plane" and the effects of "differences in effective indices of refraction on an off-diagonal Jones Matrix ratio, (eg. ((Tps/Tpp) and (Tsp/Tss) and (Tps/Tss) and (Tsp/Tpp))" respectively, by demonstrating the effect of a physical orientation, as was possible in the case Berek-type retarders/compensators. That is, in the case of a Berek-type retarder/compensator, it is possible to relatively easy to describe separate effects which occur when an optical axis which deviates from precisely perpendicular to an alignment surface is oriented so that it is in exclusively in the "P" or exclusively in the "S" plane. As a Berek-type retarder/compensator is then caused to "tilt" through a number of "tilt" angles in the "P" plane, thereby effecting a number of Angles-of-Incidence in the "P" plane between an incident polarized beam of electromagnetic radiation and an alignment surface it is relatively easy to understand how an optical axis projected exclusively in the "P" or "S" plane will effect a polarized beam of electromagnetic radiation caused to interact therewith. Where a non-Berek-type retarder/compensator is utilized, however, there is no equivalent easy way to "separate out" the effects of "shifted data symmetry" and "different indices of refraction" by a simple description of the effects of a physical alignment. As mentioned, while an optical axis in a non-Berek-type retarder/compensator does not typically deviate from coincidence with a radially oriented projection, it is a concern that a radially oriented optical axis can be oriented other than parallel to an alignment surface, and the present invention allows evaluation of an amount of deviation of an optical axis in a non-Berek-type retarder/compensator from a parallel orientation with an alignment surface. Again, this requires that the rotation direction of a radially oriented optical axis be known, or that additional data for simultaneously determining it must be acquired and included in a regression procedure for determining Jones matrix component ratios, (which mediate evaluation of deviation of a radially directed optical axis away from being parallel with said alignment surface).

Continuing, just as in the case where deviation of an optical axis from ideal orientation in a Berek-type retarder/compensator is determined utilizing data obtained during various "tilts" in a "P" plane, the present invention utilizes data acquired at various "P" plane "tilt" angles to, in a regression procedure, determine deviation of an optical axis from an orientation parallel to an alignment surface in a non-Berek-type retarder/compensator, but also requires that data be acquired at a number of Wavelengths, (or possibly at a number of rotation angles of a non-Berek-type retarder/compensator around an axis perpendicular to an alignment surface thereof), to provide sufficient data to simultaneously allow determination of the rotated angular direction of a radially oriented optical axis therein. Again, the extra data obtained by, typically, use of a multiplicity of wavelengths in conjunction with three (3) angles of incidence of a polarized beam of electromagnetic radiation with respect to an alignment surface is required to identify the angular direction of a radially oriented optical axis in a non-Berek-type retarder/compensator, (which has no analogically equivalent unknown in the case of a Berek-type retarders/compensators, wherein the direction of the optical axis in known to be generally perpendicular to an alignment surface).

Whether a Berek-type or non-Berek-type retarder/compensator is investigated by the present invention method, it is to be understood that a model for the retarder/compensator typically contains three calibration parameters which must be evaluated by regression onto experimentally determined numerical values for on-diagonal and/or off-diagonal ratios. The calibration parameters typically include a thickness, (which is on the order of one (1) to two (2) Mils in the type of crystalline material retarders/compensators to which the present invention can be relatively easily applied), and deviation angle(s) from ideal, which deviation angle(s) are determined by difference in indices of refraction "seen" by "P" and "S" components of a polarized beam of electromagnetic radiation caused to be transmitted through a crystalline material retarder/compensator. In a Berek-type retarder/compensator two (2) deviation angle calibration angles are generally necessary to describe the deviation in direction of an optical axis away from coincidence with a perpendicular to an alignment surface in "P" and "S" directions. In the case of a non-Berek-type retarder/compensator generally only one (1) deviation angle calibration parameter is necessary to describe the deviation in direction of an optical axis away from a parallel orientation with respect to an alignment surface, but do recall that an angular direction of said radially oriented optic axis must also be found. (Note, in some cases a known thickness can be used and the number of calibration parameters reduced to two (2) in both the Berek-type, and non-Berek-type retarder/compensator cases, and in the non-Berek-type case if the angular direction of a radially oriented optical is predetermined by known physical alignment, only one (1) calibration parameter remains to be evaluated).

The present invention method, in the case of a Berek-type retarder/compensator, typically involves regression of a mathematical model composed of thickness and deviation angles, (from a perpendicular to an alignment surface), in "P" and "S" directions as calibration parameters, onto experimentally obtained magnitudes of an on-diagonal ratio (Tpp/Tss) at a plurality of "P" plane "tilts", (which allows determining a "reduced-square-error" most likely value for deviation of an optical axis from a perpendicular to an alignment surface in a "P" plane direction), and simultaneous regression onto experimentally obtained magnitudes of an off-diagonal ratio selected from the group consisting of ((Tps/Tpp) and (Tsp/Tss) and (Tps/Tss) and (Tsp/Tpp)) at said plurality of "P" plane "tilts", (which allows determining a "reduced-square-error" most likely value for deviation of an optical axis from a perpendicular to an alignment surface in a "S" plane direction. At each angle-of-incidence there is also available additional experimentally obtained data in the form of a measured retardation phase shift entered between orthogonal components of a polarized beam of electromagnetic radiation caused to be transmitted through said Berek-type retarder/compensator. Said phase shift angle can be utilized to provide "real" and "imaginary" parts of on-diagonal and off-diagonal ratios identified infra, and said regression procedure can be performed using only "real", only "imaginary" or both "real" and "imaginary" parts of a ratio. It is also noted that "real" and/or "imaginary" parts of more than one off-diagonal ratio can be utilized.

In the case where a non-Berek-type retarder/compensator, regression of a model composed of thickness and a deviation angle, (of an optical axis from parallel with respect to an alignment surface) and typically a "radial angular direction location", as calibration parameters, onto experimentally obtained magnitudes of on-diagonal ratio (Tpp/Tss) and simultaneously onto experimentally obtained magnitudes of an off-diagonal ratio selected from the group consisting of ((Tps/Tpp) and (Tsp/Tss) and (Tps/Tss) and (Tsp/Tpp)) determined at a plurality of "P" plane "tilts" and a plurality of Wavelengths allows determining "reduced-square-error" most likely values for the radial directed angle (ie. rotation position), of a radially directed optical axis, and for said deviation angle of an optical axis from a parallel to an alignment surface. As in the Berek-type retarder/compensator case, at each angle-of-incidence there is also available additional experimentally obtained data in the form of an ellipsometrically measured retardation phase shift entered between orthogonal components of a polarized beam of electromagnetic radiation caused to be transmitted through said Berek-type retarder/compensator. Said phase shift angle can be utilized to provide "real" and "imaginary" parts of on-diagonal and off-diagonal ratios identified infra, and said regression procedure can be performed using only "real", only "imaginary" or both "real" and "imaginary" parts of a ratio. It is also noted that "real" and/or "imaginary" parts of more than one off-diagonal ratio can be utilized.

It is specifically pointed out that, regarding application to the Berek-type retarder/compensator, it is determination of the value for deviation of an optical axis from a perpendicular orientation with respect to an alignment surface in "P" and "S" plane direction which is the most significant achievement of the present invention. In the case where a non-Berek-type retarder/compensator is investigated it is determination of the value for deviation of a radially directed optical axis from a parallel orientation with respect to an alignment surface which is the most significant achievement of the present invention.

Said significant present invention achievements are enabled by the ability to experimentally measure a total retardation phase angle affected between related orthogonal components of a polarized beam of electromagnetic radiation caused to be transmitted through a crystalline material. As mentioned infra herein, a typical Berek-type or non-Berek-type retarder/compensator is on the order of one (1) to two (2) mils thick. A polarized electromagnetic beam of a wavelength of hundreds to thousands of nanometers which is caused to pass therethrough, and which encounters different refractive indices for the "P" and "S" components, will have upwards of one-tenth ($1/10$) of a degree retardence imposed between said "P" and "S" components by the difference in refractive indices which the "P" and "S" components "see". This amount of imposed retardation between "P" and "S" orthogonal components on a per cycle basis can be very accurately determined to eight (8) or nine (9) decimal places based upon a measurement of a summed total phase delay effected in a polarized electromagnetic beam which exits a retarder/compensator material system. It is this accuracy in measurement which allows the accurate determination, via a regression based procedure, of deviation of an optical axis away from coincidence with a perpendicular to an alignment surface in a "P" and "S" planes in Berek-type retarder/compensators, and the accurate determination of deviation of an optical axis away from coincidence with a parallel to an alignment surface in non-Berek-type retarder/compensators. Again, were absolute values for two refractive indices required to be determined separately and then used in determining deviation of an optical axis from a desired perpendicular (parallel) orientation with respect to a Berek-type "P" and "S" planes (non-Berek-type) retarder/compensator alignment surface, rather than determination of a single (difference in refractive indices), it would not be possible to determine with accuracy deviation of an optical axis from coincidence with a perpendicular to an alignment surface in a "P" and "S" planes in a Berek-type retarder/compensator and deviation of an optical axis from parallel coincidence in a non-Berek-type retarder/compensator.

It is further elaborated that experimentally determined magnitudes for on-diagonal and off-diagonal ratios are generally complex numbers, and for the purposes of practicing regression, the "real" and "imaginary" components are independent values. Thus, if it is necessary to evaluate three calibration parameters, say a thickness and two "deviation angles" (from coincidence with an ideally directed optical axis in "P" and "S" directions), in a model of a Berek-type crystalline material in order to determine alignment of the optical axis thereof with respect to an alignment surface thereof, then one must at a minimum develop the equivalent of three equations which each relate experimentally measured numbers, (eg. "real" or "imaginary" parts of measured ratio(s)), to some function which includes said three calibration parameters. That is, mathematically, to uniquely determine three unknowns requires three equations. When utilizing a regression procedure to evaluate calibration parameters, however, it is typical to obtain more data than absolutely necessary, (ie. over determine), to uniquely determine the number of calibration parameters involved. That is, where three calibrations parameters are to be evaluated, many more than three "effective equations" are developed and used in a common regression. A regression procedure then provides a "reduced-square-error" "most likely" estimate of numerical values for the calibration parameters, and uses extra information available to provides "error-bars", (ie. standard deviation values), which indicate the accuracy of said most likely calibration parameter numerical values. The present invention can be practiced using a just sufficient number of effective "equations" to determine numerical values of calibration parameters which determine the desired indication of optical axis orientation with respect to an alignment surface, but the present invention is generally practiced using more than a just sufficient number of effective "equations" in a regression procedure. The amount of over-determination is not critical to practice of the invention other than in various circumstances varying amounts of over-determination might be found to provide varying degrees of accuracy of values for calibration parameters. It is to be understood that, as a result, the present invention is not limited to the use of any specific "real" and/or "imaginary" components of any specific on-diagonal and/or specific off-diagonal Jones Matrix component ratios, or combination of "real" and/or "imaginary" components of any specific on-diagonal and/or specific off-diagonal Jones Matrix component ratios. This flexibility, of course, inherently makes drafting of "definite" Claims of appropriate breadth difficult, and the Claims should be interpreted with this in mind.

Practice of the present invention generally includes providing, for a material system being investigated, two (2) known ideal material system indices of refraction for "p" and "S" directions in the plane of an alignment surface, and a third (3rd) known ideal index of refraction in a direction oriented perpendicularly to said indices of refraction in said "P" and "S" directions in said alignment surface. The method of the present invention serves to identify optical axis orientation with respect to an alignment surface consistent with "effective" indices of refraction "seen" by "P" and "S" components of an incident beam of polarized electromagnetic radiation which is caused to impinge upon a material system along a locus perpendicular to an alignment surface thereof, and transmitted through said material system, which "effective" indices of refraction result from each of said "P" and "S" components encountering more than one (1) of said known refractive index as a result of the path said incident beam of polarized electromagnetic radiation takes through said material system. Differences in encountered "effective" refractive indices "seen" by "P" and "S" components serve to effect an ellipsometrically measurable polarization state "phase angle" retardation difference effected between said "P" and "S" components of said incident beam of polarized electromagnetic radiation data, which data enables determination of the orientation of an optical axis with respect to an alignment surface of said material system which accounts for said "effective" refractive indices. If an optical axis is, for instance, oriented precisely perpendicular to an alignment surface in a material system, then the "effective" indicies of refraction "seen" by "P" and "S" components of a polarized beam of electromagnetic radiation which impinges on the alignment surface of said material system along a locus perpendicular to said alignment surface will be the ideal materials system values. Where an ideal Berek-type optical retarder/compensator is the material system, said indicies of refraction "seen" by said "P" and "S" components are equal to one another, thus no retardation "phase-angle" will be entered between said "P" and "S" components as said polarized beam of electromagnetic radiation is caused to pass through said ideal Berek-type optical retarder/compensator. If a retardation "phase-angle" is effected between said "P" and "S" components, then it is reasonable to assume, (absent the effects of stress in the Berek-type optical retarder/compensator being investigated), the optical axis is not aligned precisely with a locus perpendicular to said alignment surface. The present invention provides an ellipsometric based approach to determining the alignment of an optical axis with respect to an alignment surface of a material system, and mediates said determination of said optical axis orientation with the evaluation of material system representing transmission Jones matrix component ratios, to provide orthogonal component calibration parameters which identify optical axis direction deviation from an "ideal" optical axis orientation.

A method of qualifying material systems as having an optical axis oriented in a desired locus with respect to an alignment surface thereof can then comprise, in a functional order, the steps of:

a. by ellipsometric techniques determining the magnitude(s) of at least one member of the group consisting of: (real, imaginary and a combination of real and imaginary components), for at least one ratio of components of a material system representing transmission Jones matrix as a function of at least one member of the group consisting of: (wavelength and "P" plane angle-of-incidence of an investigating polarized beam of electromagnetic radiation to an alignment surface of said material system and optical axis radial direction rotation angle), said at least one ratio of material system representing transmission Jones matrix components being selected from the group consisting of: (on-diagonal ratio (Tpp/Tss);

and off-diagonal ratios (Tsp/Tss);

(Tps/Tss);

(Tsp/Tpp);

(Tps/Tpp));

where Tpp, Tss, Tps and Tsp are the components of a two dimensional material system representing transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

which material system representing transmission Jones matrix describes the change in polarization state between said incident and transmitted portions of said beam of electromagnetic radiation;

b. providing a mathematical model of said material system comprising at least one deviation angle calibration parameter which represents a non-coincidence of said optical axis with a desired locus with respect to said alignment surface, said mathematical model serving to relate indices of refraction, thickness and optical axis direction over a range of at least one member of the group consisting of: (wavelength and "P" plane angles-of-incidence of an investigating polarized beam of electromagnetic radiation to an alignment surface of said material system and optical axis radial direction rotation angle);

c. performing a regression procedure of said mathematical model onto said magnitude of at least one member of the group consisting of (real, imaginary and a combination of real and imaginary components), of at least one step a. selected ratio of material system representing transmission Jones matrix components as a function of at least one member of the group consisting of: (wavelength and "P" plane angle-of-incidence of an investigating polarized beam of electromagnetic radiation to an alignment surface of said material system and optical axis radial direction rotation angle), such that said at least one deviation angle calibration parameter is evaluated;

d. selecting acceptable range(s) of value(s) for said at least one direction deviation angle calibration parameter(s) and accepting as qualified a material system with value(s) for said at least one direction deviation angle calibration parameter(s), within said selected acceptable range(s).

Said method of qualifying material systems can further comprise the step of:

e. plotting magnitude(s) of determined on-diagonal (Tpp/Tss) and/or off-diagonal ratio(s) selected from the group consisting of: ((Tps/Tpp) and (Tsp/Tss) and (Tps/Tss) and (Tsp/Tpp)), with respect to at least one parameter selected from the group consisting of: (wavelength and "P" plane angle-of-incidence of said polarized beam of electromagnetic radiation to said alignment surface and optical axis radial direction rotation angle), and accepting said material system based upon observing said plots only if said plot(s) essentially match known "template" plots.

A method of qualifying material systems as having an optical axis oriented perpendicular to an alignment surface thereof can comprise, in a functional order, the steps of:

a. selecting a wavelength of electromagnetic radiation and aligning a material system such that an incident polarized beam of electromagnetic radiation of said selected wavelength is caused to impinge upon an alignment surface of said material system with an angle-of-incidence in a "P" plane, and such that a portion of said beam of electromagnetic radiation is caused to be transmitted through said material system;

b. selecting a plurality of "P" plane angles-of-incidence of said incident polarized beam of electromagnetic radiation with respect to said alignment surface and for said plurality of "P" plane angles-of-incidence, determining by ellipsometric techniques:

the complex magnitude of at least one material system representing transmission Jones matrix component ratio selected from the group consisting of: (on-diagonal ratio (Tpp/Tss)

and off-diagonal ratios (Tps/Tpp);
(Tsp/Tss);
(Tps/Tss);
(Tsp/Tpp));

where Tpp, Tss, Tps and Tsp are the components of a two dimensional material system representing transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

which material system representing transmission Jones matrix describes the change in polarization state between said incident and transmitted portions of said beam of electromagnetic radiation;

c. providing a mathematical model for said material system comprising "P" and "S" direction deviation angle calibration parameters, said mathematical model serving to relate material system indices of refraction, thickness and optical axis direction orientation at a plurality of wavelengths and incident polarized beam of electromagnetic radiation angles-of-incidence with respect to said alignment surface; appropriate values of which "P" and "S" direction deviation angle calibration parameters serve to make said model internally consistent with respect to:

the complex magnitude of said at least one material system representing transmission Jones matrix component ratio selected from the group consisting of: (on-diagonal ratio (Tpp/Tss), and off-diagonal ratios, (Tps/Tpp), (Tsp/Tss), (Tps/Tss), (Tsp/Tpp));

d. performing a mathematical regression of the mathematical model onto:

the magnitude of at least one component selected from the group consisting of: (the real part, the imaginary part and a combination of real and imaginary parts), of said at least one material system representing transmission Jones matrix component ratio selected from the group consisting of: (on-diagonal ratio (Tpp/Tss) and off-diagonal ratios (Tps/Tpp), (Tsp/Tss), (Tps/Tss), (Tsp/Tpp), as a function of "P" plane angle-of-incidence of said beam of electromagnetic radiation with respect to said alignment surface), the purpose of said mathematical regression being to determine reduced square error numerical values for said "P" and "S" direction deviation angle calibration parameters, said "P" and "S" direction deviation calibration parameters being angular offsets of said optical axis from an ideal perpendicular orientation to said alignment surface in said "P" and "S" orthogonal directions respectively; and e. selecting an acceptable range of values for each of said "P" and "S" direction deviation angle calibration parameters and accepting as qualified a material system with values for said "P" and "S" direction deviation angle calibration parameters, within said selected acceptable ranges.

Said method of qualifying material systems which ideally have an optical axis oriented perpendicular to an alignment surface thereof can further comprise at least one step selected from the following steps f. and g.:

f. plotting magnitudes of at least one of said ratios determined in step b. with respect to angle-of-incidence of said polarized beam of electromagnetic radiation to said alignment surface and accepting said material system based upon observing said plot(s) only if a plot for an on-diagonal ratio (Tss/Tpp) is symmetrical around an angle-of-incidence of said polarized beam of electromagnetic radiation to said alignment surface which results when said polarized beam of electromagnetic radiation is essentially coincident with a normal to said alignment surface, and determined off-diagonal ((Tps/Tpp) and (Tsp/Tss) and (Tps/Tss) and (Tsp/Tpp)), ratio(s) are essentially zero (0.0) over the entire range of said angles-of-incidence of said polarized beam of electromagnetic radiation to said alignment surface;

g. plotting magnitude(s) of at least one determined on-diagonal (Tpp/Tss) and/or off-diagonal ratio(s) selected from the group consisting of: ((Tps/Tpp) and (Tsp/Tss) and (Tps/Tss) and (Tsp/Tpp)), with respect to angle-of-incidence of said polarized beam of electromagnetic radiation to said alignment surface, and accepting said material system based upon observing said plots only if said plot(s) essentially match known "template" plot(s) over the entire range of said angles-of-incidence of said polarized beam of electromagnetic radiation to said alignment surface.

A method of qualifying material systems as having an optical axis oriented radially in, and parallel to an alignment surface thereof can comprise, in a functional order, the steps of:

a. aligning a material system such that an incident polarized beam of electromagnetic radiation is caused to impinge upon an alignment surface of said material system with an angle-of-incidence in a "P" plane, and such that a portion of said beam of electromagnetic radiation is caused to be transmitted through said material system;

b. selecting a plurality of wavelengths and selecting a plurality of "P" plane angles-of-incidence of said incident polarized beam of electromagnetic radiation with respect to said alignment surface and for said plurality of wavelengths and plurality of "P" plane angles-of-incidence, determining by ellipsometric techniques:
the complex magnitude of at least one material system representing transmission Jones matrix component ratio selected from the group consisting of: (on-diagonal ratio
(Tpp/Tss);
and off-diagonal ratios
(Tps/Tpp);
(Tsp/Tss);
(Tps/Tss);
(Tsp/Tpp));
where Tpp, Tss, Tps and Tsp are the components of a two dimensional materials system representing transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

which materials system representing transmission Jones matrix describes the change in polarization state between said incident and transmitted portions of said beam of electromagnetic radiation;

c. providing a mathematical model for said material system comprising "radial angular direction location" and "deviation from parallel to alignment surface plane deviation angle" calibration parameters, said mathematical model serving to relate material system indices of refraction, thickness and optical axis orientation at a plurality of wavelengths and incident polarized beam of electromagnetic radiation angles-of-incidence, appropriate values of which "radial angular direction location" and "deviation from parallel to alignment surface plane deviation angle" calibration parameters serve to make said model internally consistent with respect to:
the complex magnitude of said at least one materials system representing transmission Jones matrix component ratio selected from the group consisting of: (on-diagonal ratio (Tpp/Tss) and off-diagonal ratios (Tps/Tpp), (Tsp/Tss), (Tps/Tss), (Tsp/Tpp));

d. performing a mathematical regression of the mathematical model onto:
the magnitude of at least one component selected from the group consisting of: (the real part, the imaginary part and a combination of real and imaginary parts), of said at least one material system representing transmission Jones matrix component ratio selected from the group consisting of: (on-diagonal ratio (Tpp/Tss) and off-diagonal ratios (Tps/Tpp), (Tsp/Tss), (Tps/Tss) (Tsp/Tpp), as a function of wavelength and of "P" plane angle-of-incidence of said polarized beam of electromagnetic radiation with respect to said alignment surface), the purpose of said mathematical regression being to determine reduced square error numerical values for said "radial angular direction location" and "deviation from parallel to alignment surface plane deviation angle" calibration parameters, said "deviation from parallel to alignment surface plane deviation angle" calibration parameter being an angular offset of said optical axis from an ideal parallel orientation to said alignment surface; and e. selecting an acceptable range of values for said "deviation from parallel to alignment surface plane deviation angle" and accepting as qualified a material system with a value for said "deviation from parallel to alignment surface plane deviation angle" calibration parameter, within said selected acceptable range.

Said method of qualifying material systems which ideally have an optical axis oriented radially in, and parallel to an alignment surface thereof can further comprise the step of:

f. plotting magnitudes of at least one determined on-diagonal (Tpp/Tss) and/or off-diagonal ratio(s) selected from the group consisting of: ((Tps/Tpp) and (Tsp/Tss) and (Tps/Tss) and (Tsp/Tpp)), with respect to wavelength at at least one angle-of-incidence of said polarized beam of electromagnetic radiation to said alignment surface, and accepting said material system based upon observing said plot(s) only if said plot(s) essentially match known "template" plot(s) over the entire range of said wavelengths.

Another method of qualifying material systems which ideally have an optical axis oriented radially in, and parallel to an alignment surface thereof can comprise, in a functional order, the steps of:

a. aligning a material system such that an incident polarized beam of electromagnetic radiation is caused to impinge upon an alignment surface of said material system with an angle-of-incidence in a "P" plane, and such that a portion of said beam of electromagnetic radiation is caused to be transmitted through said material system;

b. selecting a plurality of optical axis radial direction rotation angles and selecting a plurality of "P" plane angles-of-incidence of said incident polarized beam of electromagnetic radiation with respect to said alignment surface and for said plurality of optical axis radial direction rotation angles and plurality of "P" plane angles-of-incidence, determining by ellipsometric techniques:

the complex magnitude of at least one material system representing transmission Jones matrix component ratio selected from the group consisting of: (on-diagonal ratio
(Tpp/Tss)
and off-diagonal ratios
(Tps/Tpp);
(Tsp/Tss);
(Tps/Tss);
(Tsp/Tpp));
where Tpp, Tss, Tps and Tsp are the components of a two dimensional material system representing transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

which material system representing transmission Jones matrix describes the change in polarization state between said incident and transmitted portions of said beam of electromagnetic radiation;

c. providing a mathematical model for said material system comprising "radial angular direction location" and "deviation from parallel to alignment surface plane deviation angle" calibration parameters, said mathematical model serving to relate material system indices of refraction, thickness and optical axis orientation at a plurality of optical axis radial direction rotation angles and incident polarized beam of electromagnetic radiation angles-of-incidence with respect to said alignment surface, appropriate values of which "radial angular direction location" and "deviation from parallel to alignment surface plane deviation angle" calibration parameters serve to make said model internally consistent with respect to:

the complex magnitude of said at least one material system representing transmission Jones matrix component ratio selected from the group consisting of: (on-diagonal ratio (Tpp/Tss) and off-diagonal ratios (Tps/Tpp), (Tsp/Tss), (Tps/Tss), (Tsp/Tpp));

d. performing a mathematical regression of the mathematical model onto:

the magnitude of at least one component selected from the group consisting of: (the real part, the imaginary part and a combination of real and imaginary parts), of said at least one material system representing transmission Jones matrix component ratio selected from the group consisting of: (on-diagonal ratio (Tpp/Tss) and off-diagonal ratios (Tps/Tpp), (Tsp/Tss), (Tps/Tss), (Tsp/Tpp), as a function of optical axis radial direction rotation angle and of "P" plane angle-of-incidence of said polarized beam of electromagnetic radiation with respect to said alignment surface), the purpose of said mathematical regression being to determine reduced square error numerical values for said "radial angular direction location" and "deviation from parallel to alignment surface plane deviation angle" calibration parameters, said "deviation from parallel to alignment surface plane deviation angle" calibration parameter being an angular offset of said optical axis from an ideal parallel orientation to said alignment surface; and e. selecting an acceptable range of values for said "deviation from parallel to alignment surface plane deviation angle" and accepting as qualified a material system with a value for said "deviation from parallel to alignment surface plane deviation angle" calibration parameter, within said selected acceptable range.

Said method of qualifying material systems which ideally have an optical axis oriented radially in, and parallel to an alignment surface thereof can further comprise the step of:

f. plotting magnitudes of at least one determined on-diagonal (Tpp/Tss) and/or off-diagonal ratio(s) selected from the group consisting of: ((Tps/Tpp) and (Tsp/Tss) and (Tps/Tss) and (Tsp/Tpp)), with respect to optical axis radial direction rotation angles at at least one angle-of-incidence of said polarized beam of electromagnetic radiation to said alignment surface, and accepting said material system based upon observing said plot(s) only if said plot(s) essentially match known "template" plot(s) over the entire range of said optical axis radial direction rotation angles.

A further method of qualifying material systems which ideally have an optical axis oriented in a desired locus with respect to an alignment surface thereof can comprise, in a functional order, the steps of:

a. by ellipsometric techniques determining the magnitude(s) of at least one member of the group consisting of: (real, imaginary and a combination of real and imaginary components), for at least one ratio of components of a material system representing transmission Jones matrix as a function of at least one member of the group consisting of: (wavelength and "P" plane angle-of-incidence of an investigating polarized beam of electromagnetic radiation to an alignment surface of said material system and optical axis radial direction rotation angle), said at least one ratio of material system representing transmission Jones Matrix components being selected from the group consisting of: (on-diagonal ratio (Tpp/Tss);

and off-diagonal ratios (Tsp/Tss);
(Tps/Tss);
(Tsp/Tpp);
(Tps/Tpp));

where Tpp, Tss, Tps and Tsp are the components of a two dimensional material system representing transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

which material system representing transmission Jones matrix describes the change in polarization state between said incident and transmitted portions of said beam of electromagnetic radiation;

b. plotting magnitude(s) of at least one determined on-diagonal (Tpp/Tss) and/or off-diagonal ratio(s) selected from the group consisting of: ((Tps/Tpp) and (Tsp/Tss) and (Tps/Tss) and (Tsp/Tpp)), with respect to at least one parameter selected from the group consisting of: (wavelength and "P" plane angle-of-incidence of said polarized beam of electromagnetic radiation to said alignment surface and optical axis radial direction rotation angle), and accepting said material system based upon observing said plot(s) only if said plot(s) essentially match known "template" plot(s).

Any of the recited methods of qualifying material systems as having an optical axis oriented in a desired locus with respect to an alignment surface thereof, (eg. perpendicularly to an alignment surface, or radially from a central point and parallel to an alignment surface), can include the alignment of said material system such that an incident beam of electromagnetic radiation caused to impinge upon a alignment surface thereof in a "P" plane effects an initial angle-of-incidence along a locus essentially normal to said alignment surface, and includes causing said incident beam of electromagnetic radiation to pass through a centrally located aperture in a quadrant detector, monitoring said portion of said incident beam of electromagnetic radiation is caused to reflect essentially perpendicularly back from said alignment surface with said quadrant detector, and adjusting said angle-of-incidence of said incident beam of electromagnetic radiation with respect to said alignment surface of said material system such that each quadrant of said quadrant detector detects an essentially equal magnitude of said reflected incident beam of electromagnetic radiation.

The method of qualifying material systems as having an optical axis oriented in a desired locus with respect to an alignment surface thereof, (eg. perpendicularly to an alignment surface, or radially from a central point and parallel to an alignment surface), can effect determination of the complex magnitude of at least one material system representing transmission Jones matrix component ratio selected from the group consisting of: (on-diagonal ratio (Tpp/Tss) and off-diagonal ratios (Tps/Tpp), (Tsp/Tss), (Tps/Tss), (Tsp/Tpp)); by a procedure comprising the steps of:

b1. setting the polarization state of said incident beam of electromagnetic radiation;

b2. monitoring the polarization state of said portion of said beam of electromagnetic radiation which is caused to be transmitted through said material system;

b3. selecting a plurality of "P" plane angles-of-incidence of said incident polarized beam of electromagnetic radiation with respect to said alignment surface, and optionally a member of the group consisting of: (a plurality of wavelengths and a plurality of optical axis radial direction rotation angle);

and repeating steps b1. and b2. for said plurality of "P" plane angles-of-incidence and optionally a member of the group consisting of: (a plurality of wavelengths and a plurality of optical axis radial direction rotation angle);

b4. selecting monitored "P" plane angles-of-incidence and at said selected "P" plane angles-of-incidence and optionally a member of the group consisting of: (a plurality of wavelengths and a plurality of optical axis radial direction rotation angle), and determining material system properties from polarization states of said set incident and monitored beam of electromagnetic radiation transmitted through said material system;

b5. repeating steps b1. through b4. utilizing different settings of polarization state in step b1. and mathematically determining, at said step b4. selected monitored "P" plane angles-of-incidence and optionally a member of the group consisting of: (a plurality of wavelengths and a plurality of optical axis radial direction rotation angle), the complex magnitude of at least one material system representing transmission Jones matrix component ratio selected from the group consisting of: (on-diagonal ratio (Tpp/Tss) and off-diagonal ratios (Tps/Tpp), (Tsp/Tss), (Tps/Tss), (Tsp/Tpp)).

The important aspects of the method of the present invention just described are shown in FIG. 11 in Flow Chart form.

Finally, it is to be understood that a mathematical model for a material system as refered to herein is generally comprised of parameters such as thickness, indicies of refraction in three orthogonal directions, and deviation angle calibration parameter(s) between an ideal optical axis direction with respect to an alignment surface and a locus of a direction actually ocupied by an optical axis in a specific material system. The mathematical model utilizes obvious Trigonometric relationships between alignment surface and ideal optical axis direction and between ideal optical axis direction and actual optical axis loci direction in a particular material system, as well as well known optics relationships such as demonstrated by Snell's Law, and angle of incidence equals angle of reflection and the effects of changing refractive index on a beam of electromagnetic radiation caused to pass through a material system comprised of a number of sequentially encountered refractive indicies. The addition of, and evaluation of, deviation angle calibration parameter(s) between an ideal optical axis direction with respect to an alignment surface and a locus of a direction actually ocupied by an optical axis in a specific material system, is what distinguishes the present invention over mathematical models which can be found described in references such as the previously cited book by Azzam and Bashara, which reference is incorporated by reference herein. In addition, the J. A. Woollam Co. WVASE Instruction Manual, which provides insight to material system mathematical modeling and regression based evaluation of mathematical model parameters, is further incorporated by reference herein, as is a book by Halliday and Resnick titled "Physics", published by Wiley in 1965.

The present invention will be better understood by reference to the Detailed Description Section of this Disclosure, in conjunction with the Drawings.

SUMMARY OF THE INVENTION

It is a purpose of the present invention to teach a method of qualifying material systems such as uni-axial and bi-axial crystalline materials as sufficiently ideal for practical usage.

It is another particularly important purpose of the present invention to teach a method for identifying optical compensators/retarders which have an optical axis oriented as desired with respect to an alignment surface thereof.

It is yet another purpose of the present invention to teach a method for identifying material systems which have an optical axis which is ideally oriented perpendicular to, as well as to material systems which have an optical axis ideally oriented in the plane of, an alignment surface thereof.

It is yet still another purpose of the present invention to teach a method by which the alignment of an optical axis with respect to an ideal in a material system, can be identified to within a hundredth of a degree.

It is another purpose of the present invention to teach application thereof to determination of the orientation of an optical axis in crystalline material Berek-type optical retarders/compensators.

It is yet another purpose of the present invention to teach application thereof to determination of the orientation of an optical axis in crystalline material non-Berek-type optical retarders/compensators.

It is still yet another purpose of the present invention to teach application thereof in original manufacture and in after market quality control settings.

BRIEF DESCRIPTION OF THE DRAWINGS

FIG. 5a shows a Physical Alignment System for use in practicing the present invention.

FIGS. 5b through 5e show a Quadrature Detector for use in aligning an Optical Retarder/Compensator such that an incident Beam of electromagnetic radiation is oriented perpendicular to a Alignment Surface thereof.

FIG. 6a shows an ellipsometer system representative of a system for carrying out the present invention method, with a Berek-type Optical Retarder/Compensator present therein.

FIG. 6b shows a "P" linearly polarized beam of electromagnetic radiation impinging upon a material system, and exiting therefrom as an elliptically polarized beam of electromagnetic radiation with both "P" and "S" components separated by a phase angle.

FIGS. 7a and 7b provide perspective views of a Berek-type Optical Retarder/Compensator which aide with visualizing how orthogonal components of a Polarized Beam of Electromagnetic Radiation can "see" a third index of refraction when an Optical Axis of said Berek-type Optical Retarder/Compensator and the locus of said Polarized Beam of Electromagnetic Radiation are not coincident.

FIGS. 7c and 7d show a material system oriented so that a "P" or "S" component of an incident polarized beam of electromagnetic radiation sees the effects of one (1) and two (2) indices of refraction, respectively.

FIG. 7e shows the effect of a change in refractive index of a material on a beam of electromagnetic radiation caused to travel therethrough.

DETAILED DESCRIPTION

Typical application of the present invention qualification method is found where the orientation of an Optical Axis of an Optical Retarder/Compensator, (which Optical Retarder/Compensator is typically, but not necessarily, achieved by appropriate cutting of bulk Crystalline Material), is to be identified with respect to an Alignment surface thereof. In the following, Berek-type Optical Retarders/Compensators, which ideally have an Optical Axis oriented perpendicular to an Alignment Surface thereof, are primarily utilized as a particularly relevant, but not limiting, example to which the present invention qualification method can be applied. Also briefly discussed, as a second non-limiting example to which the present invention qualification method can be applied, are Optical Retarders/Compensators which ideally have an Optical Axis oriented radially and parallel to an Alignment Surface thereof.

Figure 1B:
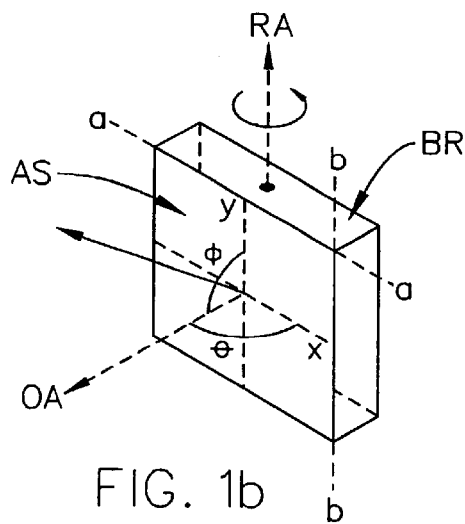
FIGS. 1a through 1d show an ideal Berek-type Optical Retarder/Compensator with a Optical Axis oriented perpendicular to a Alignment Surface thereof.
Figure 1A:
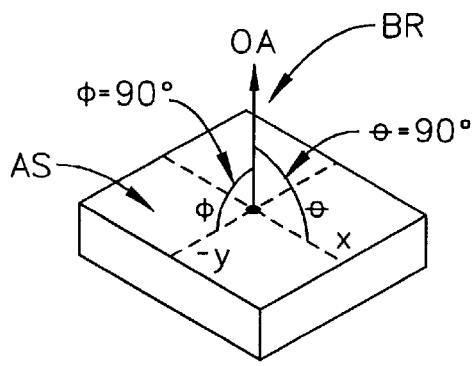
Figure 2A:
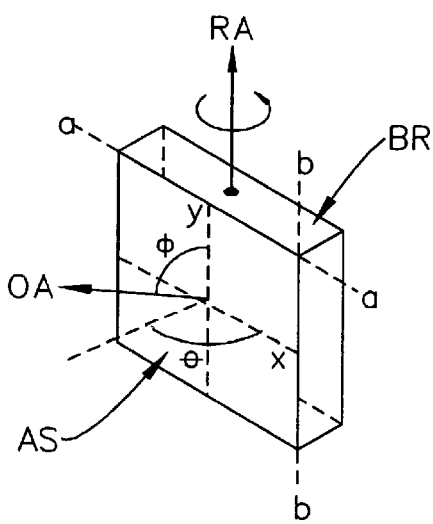
FIGS. 2a through 2c show a non-ideal Berek-type Optical Retarder/Compensator with a Optical Axis oriented other than perpendicular to a Alignment Surface thereof.
Figure 1C:
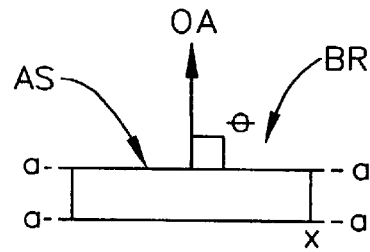
Figure 1D:
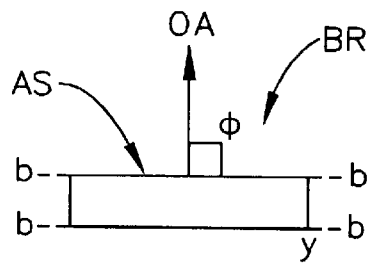
Figure 2B:
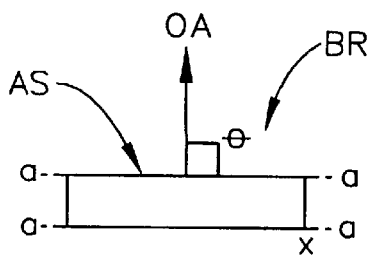
Figure 2C:
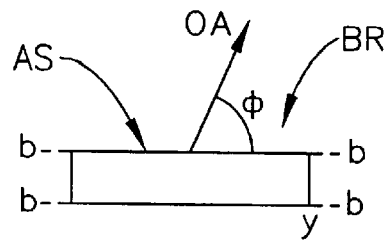
Figure 3A:
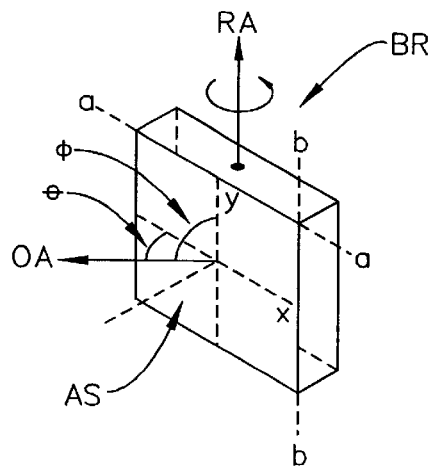
FIGS. 3a through 3c show a non-ideal Berek-type Optical Retarder/Compensator with a Optical Axis oriented other than perpendicular to a Alignment Surface thereof.
Figure 3B:
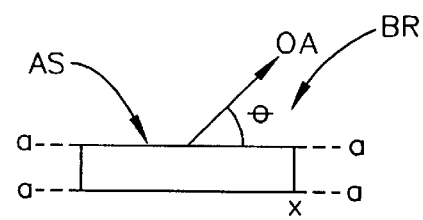
Figure 3C:
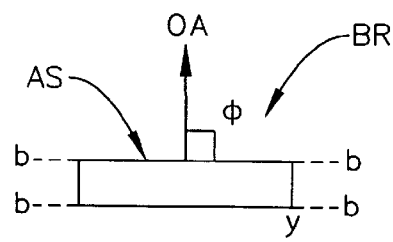

Turning now to FIGS. 1a–1d, there are shown various views of a Berek-type Optical Retarder/Compensator (BR) with its Optical Axis (OA) oriented at a desired ninety (90) degrees to the plane of an Alignment Surface (AS) thereof. For insight, FIG. 1b shows a solid arrow originating at the intersection of the "x" and "y" axes and projecting in a random direction. The ideal Optical Axis (OA) orientation in FIG. 1b is shown as a dashed line projecting perpendicular to the surface of the Berek-type Optical Retarder/Compensator. The solid arrow of FIG. 1b is shown, in FIGS. 1a, 1c and 1d, to be coincident with the ideal Optical Axis. FIGS. 2a and 3a shown that the Optical Axis (OA), which is identified by the solid arrow therein, is not always ideally coincident with an ideal perpendicular to the surface of the Berek-type Optical Retarder/Compensator as shown in FIGS. 1a, 1c and 1d. Angles (theta) and (phi) are the angles which the Optical Axis makes with respect to "X" and "Y" directions in said Alignment Surface (AS), respectively, where (theta) is shown as θ, and (phi) is shown as φ. (Note that said "X" and "Y" directions can be identified, respectively, with "P" and "S" direction when a Material System is placed in an Ellipsometer System and a Beam of Polarized Electromagnetic Radiation is caused to impinge upon an Alignment Surface thereof in a "P" plane). FIGS. 2a–2c show a non-ideal Berek-type Optical Retarder/Compensator (BR) in which the angle of the Optical Axis with respect to the "Y" direction on the Alignment Surface (AS), (ie. (phi)), is at other than ninety (90) degrees, and in which the angle of the Optical Axis (OA) with respect to the "X" direction on the Surface (AS), (ie. (theta)), is at a desired Ninety (90) degrees. FIGS. 3a–3c show a non-ideal Berek-type Optical Retarder/Compensator (BR) in which the angle of the Optical Axis (OA) with respect to the "X" direction on the Alignment Surface (AS), (ie. (theta)), is at other than ninety (90) degrees and in which the angle of the Optical Axis (OA) with respect to the "Y" direction on the Surface (AS), (ie. (phi)), is at a desired Ninety (90) degrees. Note that, as better verbally described in the Disclosure of the Invention Section, it can be easily visualized, (see FIGS. 7a and 7b to aid therewith), that a Polarized Beam of Electromagnetic Radiation caused to initially impinge upon the Berek-type Optical Retarder/Compensator (BR) Alignment Surface (AS) shown in FIG. 1a along a locus perpendicular to said Alignment Surface (AS) will "see" and be affected by two indices of refraction, (one for the "P" component and one for the "S" component. It is noted, however, that for an ideal Berek-type Optical Retarder/Compensator (BR) where a Polarized Beam of Electromagnetic Radiation is caused to impinge upon the Alignment Surface (AS) along a locus perpendicular to said Alignment Surface (AS), the refractive indices "seen" by the "P" and "S" components, are of the same value, hence a Berek-type Optical Retarder/Compensator (BR) can be adjusted in physical orientation in an ellipsometer to appear as if it is not present in that no relative retardation is entered between said Polarized Electromagnetic Beam "P" and "S" components, except for an imposed minor, normally negligible, attenuation effect.

As mentioned, FIGS. 2a–2c and 3a–3c show two versions of imperfect Berek-type Optical Retarders/Compensators (BR). In particular, note that FIG. 2a shows a Berek-type Optical Retarder/Compensator (BR) with an Optical Axis (OA) oriented with the identified angle (theta) set to ninety (90) degrees with respect to the Alignment Surface (AS) and with the angle identified as (phi) set to some angle other than ninety (90) degrees with respect to said Alignment Surface. Also note that FIG. 3a shows a Berek-type Optical Retarder/Compensator (BR) with an Optical Axis (OA) oriented with the identified angle (phi) set to ninety (90) degrees with respect to the Alignment Surface (AS) and with the angle identified as (theta) set to some angle other than ninety (90) degrees with respect to said Alignment Surface. Note that in both FIGS. 2a and 3a, however, that the same Rotation Axis (RA) is indicated as is indicated in FIG. 1a. (As described in more detail in the Disclosure of the Invention Section, this demonstrates identification of related orthogonal axes which allow relatively easy description of how the present invention determines non-ideal Optical Axis (OA) orientation with respect to an Alignment Surface (AS)). It can be relatively easily visualized, (again, reference to FIGS. 7a and 7b might aid with this), that if a Beam of Electromagnetic Radiation is caused to impinge upon the non-ideal Berek-type Optical Retarder/Compensator (BR) shown in FIG. 2a, along a locus which is initially oriented perpendicular to said Alignment Surface (AS) thereof, then said Beam of Electromagnetic Radiation will "see" and be affected by two indices of refraction as said Berek-type Optical Retarder/Compensator (BR) is caused to be rotated about the shown Rotation Axis (RA). It can also be relatively easily visualized that if a Beam of Electromagnetic Radiation is caused to impinge upon the non-ideal Berek-type Optical Retarder/Compensator (BR) shown in FIG. 3a, along a locus which is initially perpendicular to said Alignment Surface (AS) thereof, then said Beam of Electromagnetic Radiation will "see" and be affected by only one index of refraction as said Berek-type Optical Retarder/Compensator (BR) is caused to be rotated about the shown Rotation Axis (RA). (Note, in terms of "P"-"S" coordinates, the visualized Beam of Electromagnetic Radiation should be understood as being oriented in the "P" plane, which in FIG.

3a includes the Optical Axis (OA) throughout any rotation of said Berek-type Optical Retarder/Compensator (BR), clockwise or counterclockwise about Rotation Axis (RA). However, in FIG. 2a the Optical Axis (OA) is oriented in the "S" plane throughout any rotation of said Berek-type Optical Retarder/Compensator (BR), clockwise or counterclockwise about Rotation Axis (RA)).

Detection of non-ideal Optical Axis (OA) orientation, (as demonstrated by FIGS. 2a–2c and FIGS. 3a–3c), with respect to the Alignment Surface in Berek-type Optical Retarders/Compensators (BR) is a primary focus of the present invention, and when found is basis for Disqualification of the Berek-type Optical Retarder/Compensator (BR) under test. However, if an orientation of the Optical Axis (OA) with respect to the Alignment Surface (AS), (as shown in FIGS. 1a–1d), in a Berek-type Optical Retarder/Compensator (BR) under test is essentially detected by practice of the present invention, then said Berek-type Optical Retarder/Compensator (BR) is accepted as Qualified.

Figure 4A:
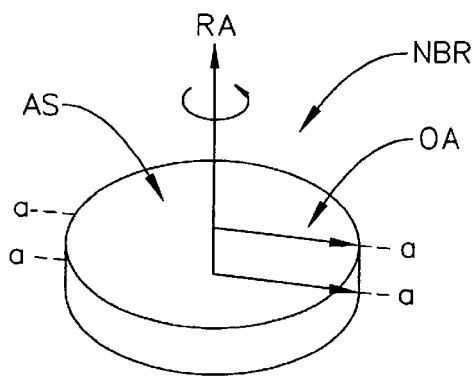
FIGS. 4a and 4b show an ideal Non-Berek Optical Retarder/Compensator with a Optical Axis oriented parallel to a Alignment Surface thereof.
Figure 4B:
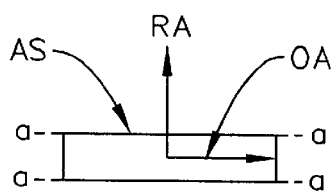
Figure 4C:
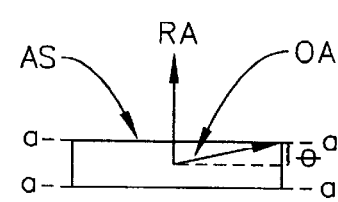
FIGS. 4c and 4d show a non-ideal Non-Berek Optical Retarder/Compensator with a Optical Axis oriented other than parallel to a Alignment Surface thereof.
Figure 4D:
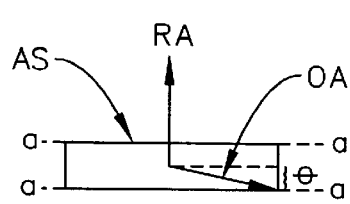

FIGS. 4a and 4b show an ideal Non-Berek-type (NBR) Retarder/Compensator in which the Optical Axis (OA) is directed radially and parallel to an Alignment Surface (AS). FIGS. 4c and 4d show non-ideal orientation of said radially oriented Optical Axis in that said Optical Axis (OA) is not parallel to the Alignment Surface (AS). Said Non-Berek-Type (NBR) Retarder/Compensator effects change in retardation entered between orthogonal components of a Beam of Polarized Electromagnetic Radiation by Rotation about Rotational Axis (RA) (which is shown to project perpendicular to the Alignment Surface (AS)) so that said Optical Axis is caused to change in Optical Axis Direction. Accurate evaluation of the angles (theta) shown in FIGS. 4c and 4d, which angles (theta) define the non-ideal Direction of said Optical Axis (OA), is a primary focus of the present invention. As described in the Disclosure Of The Invention Section herein, the method of the present invention as applied to Non-Berek-Type (NBR) Retarders/Compensators is very similar as that applied to Berek-Type (BR) Retarders/Compensators, although additional data, (typically as a function of both Angle of Incidence of said Beam of Electromagnetic Radiation with respect to an Alignment Surface and Wavelength or Optical Axis Direction Rotation Angle), must be included in the regression procedure to provide for evaluating material system transmission Jones matrix component ratios. (It is noted that an "Optical Axis Direction Rotation Angle" is effected by rotation of the FIG. 4 Non-Berek-type Retarder/Compensator about the shown Rotation Axis (RA)).

Turning now to FIG. 5a, there is shown a Physical Alignment System (PAS) for use in aligning a Berek-type Optical Retarder/Compensator (BR) such that a Beam of Electromagnetic Radiation, as shown in FIG. 5b as Electromagnetic Radiation Beam (LB), can be caused to impinge upon a Berek-type Optical Retarder/Compensator (BR) at an angle of incidence of Ninety (90) degrees. Note that the Physical Alignment System (PAS) of FIG. 5a provides Pivot Means (P1) and (P2) for allowing rotation of a Berek-type Optical Retarder/Compensator around "X" and "Y" axes. FIG. 5b shows the Berek-type Optical Retarder/Compensator (BR) in FIG. 5a, (the Physical Alignment System (PAS) shown in FIG. 5a is assumed present), and a Quadrant Detector (QD) which, in use, is caused to be present in the path of the incident Electromagnetic Radiation Beam (LB). FIG. 5c shows that said Quadrant Detector (QD), (as it would be viewed in a cross-sectional plane in FIG. 5b), in has present a Centrally Placed Aperture (CA) through which said Incident Electromagnetic Radiation Beam (LB) passes in use, and Four (4) Quadrant Detectors (Q1), (Q2), (Q3) and (Q4) which, as reference to FIG. 5b indicates, intercept a reflected portion of said Electromagnetic Radiation Beam (LB), said Reflected Portion being identified as (LBR). It should be appreciated that adjustment, (ie. appropriate rotation around Pivots (P1) and (P2)), of a Berek-type Optical Retarder/Compensator (BR) using a Physical Alignment System (PAS) as shown in FIG. 5a allows attainment of a situation wherein each of the Four Quadrants (Q1), (Q2), (Q3) and (Q4), (as shown in FIG. 5b), receive equal amounts of Reflected Electromagnetic Radiation Beam (LBR). As reflection occurs from the Alignment Surface (AS), such alignment provides that the Incident Electromagnetic Radiation Beam (LB) then approaches and impinges upon said Berek-type Optical Retarder/Compensator (BR) along a direction which is perpendicular to the Alignment Surface (AS) of said Berek-type Optical Retarder/Compensator (BR). Note that FIGS. 5e and 5d are side elevational and schematic drawings of said Quadrant Detector (QD). It is also to be noted that FIG. 6a shows a system for use in practice of the present invention will typically include a Light Source (LS), a Polarizer (PL), an Analyzer (A) and a Detector (DET), with a Berek-type (for instance) Optical Retarder/Compensator (BR) positioned therein as shown. FIG. 6b shows an incident Polarized Beam of Electromagnetic Radiation (LB), (in a purely "P" Linear Polarization State), which is being caused to impinge upon an Alignment Surface (AS) of a Material System (MAT) in a "P" plane, which Material System (MAT) can be considered to be a Berek-type Optical Retarder/Compensator (BR) or a non-Berek-type Optical Retarder/Compensator (NBR). Also shown is a Transmitted Polarized Beam of Electromagnetic Radiation (LBT) which has both "P" and "S" components, which "P" and "S" components have a "phase angle" (phi) therebetween. (Note that the symbol φ as used in FIG. 6b is distinct from the use made thereof in FIGS. 1a–1d, 2a–2c, 3a–3c and 4a–4d). Taken in combination, a ratio of the magnitudes of the "P" and "S" components and said "phase angle" (phi) constitute a Polarization State of said Transmitted Polarized Beam of Electromagnetic Radiation (LBT). FIG. 6b is included to provide a visual reference as to the effect a Material System (MAT) can have on a Polarized Beam of Electromagnetic Radiation (LB) as it is caused to be transmitted therethrough. It is also mentioned that were the Material System (MAT) a Berek-type Optical Retarder/Compensator (BR), and the incident Polarized Beam of Electromagnetic Radiation (LB) were caused to impinge upon the Alignment Surface (AS) thereof along the locus of the Optical Axis thereof, the Transmitted Polarized Beam of Electromagnetic Radiation (LBT) would be essentially unchanged, but for a typically negligible attenuation. FIG. 6b then indicates that said incident Polarized Beam of Electromagnetic Radiation (LB) is not approaching the Alignment Surface (AS) of the assumed Berek-type Optical Retarder/Compensator (BR) Material System (MAT) along the Optical Axis thereof. This might be because the Optical Axis is not aligned coincident with a perpendicular to the Alignment Surface (AS) thereof along which said incident Polarized Beam of Electromagnetic Radiation (LB) is propagating, or because the assumed Berek-type Optical Retarder/Compensator (BR) Material System (MAT) is "tilted" to intentionally cause misalignment between the locus of said incident Polarized Beam of Electromagnetic Radiation (LB) and said Optical Axis.

As alluded to infra herein, FIGS. 7a and 7b provide views, (perspective), of a Berek-type Optical Retarder/

Compensator (BR) which, when viewed in combination, can aide with visualizing how "tilting" of the shown Berek-type Optical Retarder/Compensator (BR) can cause three (3), rather than two (2), refractive indices to be "seen" by "P" and "S" components of a Polarized Beam of Electromagnetic Radiation (LB). FIG. 7a shows that "P" and "S" components of said Polarized Beam of Electromagnetic Radiation (LB) which approaches the Berek-type Optical Retarder/Compensator (BR) along a perpendicular to the Alignment Surface (AS) thereof will each "see" a single refractive index in orthogonally oriented, (ie. "P" and "S"), directions. The refractive index associated with the direction identified as "Z", however will not be "seen" by either a "P" or "S" component of the Polarized Beam of Electromagnetic Radiation (LB). FIG. 7b shows that the effect of "tilting" the Berek-type Optical Retarder/Compensator (BR) will be to bring the refractive index associated with the "Z" direction into an orientation in which the "P" and "S" components can "see" it. An off-perpendicular to Alignment Surface (AS) Optical Axis (OA) causes a similar effect, as is best appreciated by reference to FIGS. 2a and 3a. It should also be generally appreciated that where the Polarized Beam of Electromagnetic Radiation (LB) does not approach an Alignment Surface (AS) of a Berek-type Optical Retarder/Compensator (BR) along a locus aligned with the Optical Axis (OA) thereof, the "P" and "S" orthogonal components of said Polarized Beam of Electromagnetic Radiation (LB) will generally see different contributions by said third, "Z" direction, refractive index. Thus, a relative difference in retardation between "P" and "S" components is realized, (and a measurement thereof is utilized as described elsewhere in this Disclosure in determination of how an Optical Axis is oriented with respect to an Alignment Surface (AS) of an Optical Retarder/Compensator under test). FIGS. 7c and 7d provide additional visual aides wherein a "P" or "S" component of a Polarized Beam of Electromagnetic Radiation (LB) is shown entering a Material System (MAT). The Material System has an Index of Refraction perpendicular to the Alignment Surface (AS), (represented by vertically oriented lines in FIG. 7c), and one parallel thereto, (represented by horizontally oriented lines in FIG. 7c). In FIG. 7c the Material System (MAT) is oriented so that the "P" or "S" Component of the Polarized Beam of Electromagnetic Radiation (LB) is influenced only by the Index of Refraction (IR1) which is parallel to the Alignment Surface (AS), (ie. the locus of (LB) crosses only lines which are parallel to the Alignment Surface (AS)), however, in FIG. 7d the Material System (MAT) is oriented so that the "P" or "S" Component of the Polarized Beam of Electromagnetic Radiation (LB) is influenced by a combination of the Indices of Refraction which are oriented perpendicular (IR1) and parallel (IR1) to the Alignment Surface (AS), (ie. the locus of (LB) crosses lines which are both perpendicular (IR1) and parallel (IR3) to the Alignment Surface (AS)). (A Second Index of Refraction, not shown), can be considered to be projecting into and out of the page).

Figure 8:
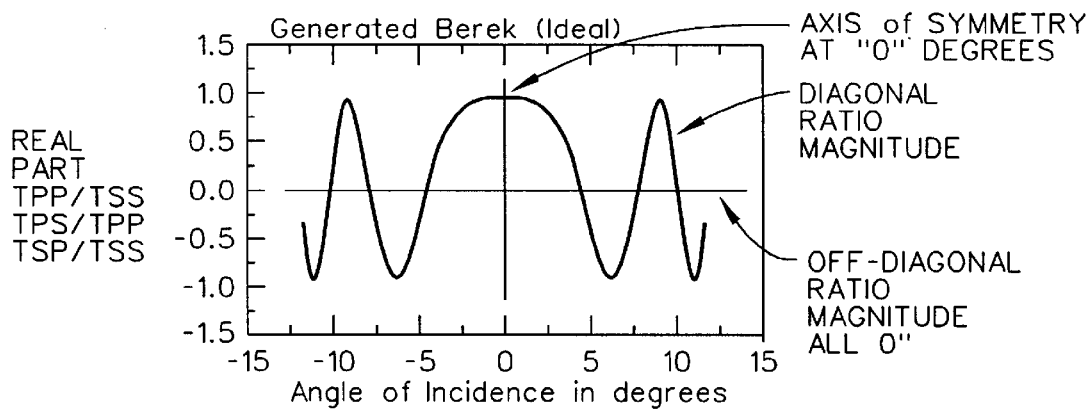
FIG. 8 shows a plot of the magnitudes of the real parts of relevant ratios of Jones Matrix elements for an ideal Berek-type Retarder/Compensator.
Figure 9:
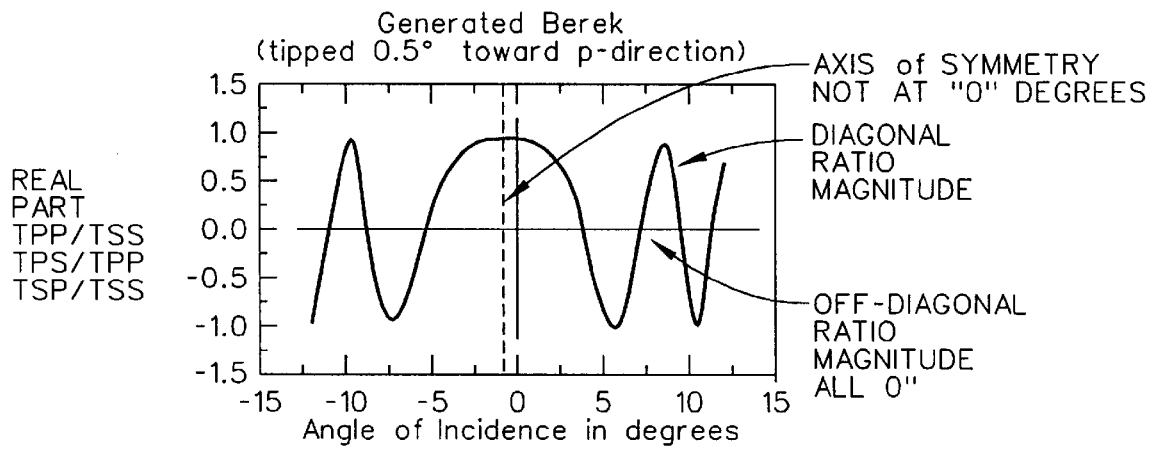
FIG. 9 shows a plot of the magnitudes of the real parts of relevant ratios of Jones Matrix elements for a non-ideal Berek-type Retarder/Compensator.
Figure 10:
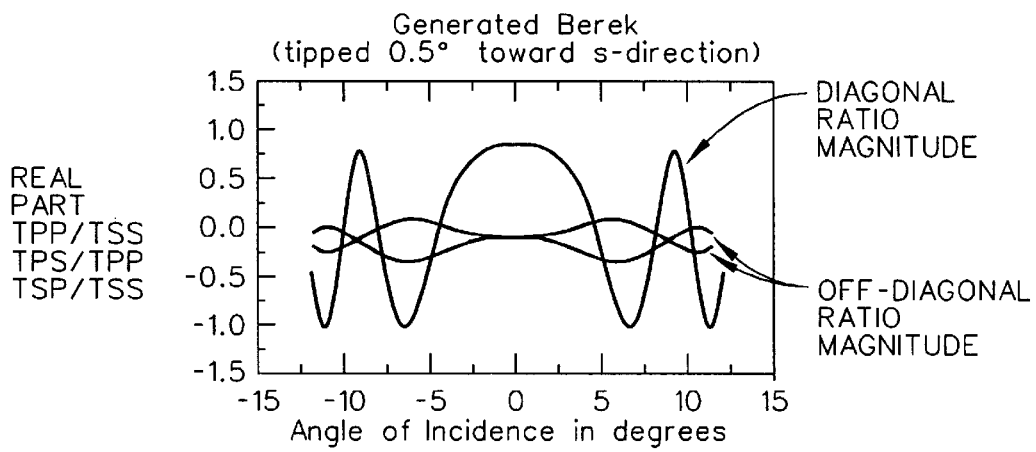
FIG. 10 shows a plot of the magnitudes of the real parts of relevant ratios of Jones Matrix elements for a non-ideal Berek-type Retarder/Compensator.
Figure 11:
FIG. 11 is a flow chart of important steps of a method of the present invention.
Figure 11:
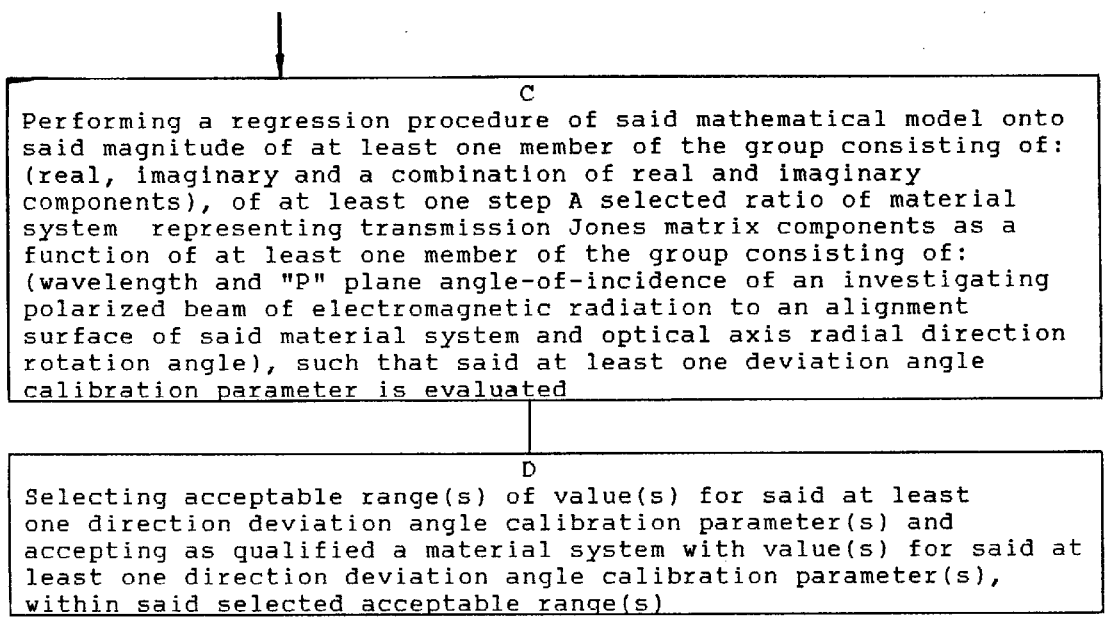

Turning now to FIGS. 8, 9 and 10, there are shown graphical results of practicing the present invention using ideal, and two versions of non-ideal Berek-type Optical Retarders/Compensators (BR). As shown in FIGS. 1a–1d, ideal Berek-type Optical Retarders/Compensators (BR) present with their Optical Axis (OA) oriented perpendicular to the Alignment Surface (AS) thereof, and non-ideal Berek-type Optical Retarders/Compensators (BR) have their Optical Axis (OA) oriented other than perpendicular to the Alignment Surface (AS) thereof, (see FIGS. 2a–2c and 3a–3c). After alignment of a Berek-type Optical Retarder/Compensator (BR), as described with respect to FIGS. 5a and 6a, so that an Incident Electromagnetic Radiation Beam (LB) impinges upon said Berek-type Optical Retarder/Compensator (BR) along a pathway oriented perpendicular to the Alignment Surface (AS) of said Berek-type Optical Retarder/Compensator (BR), said Berek-type Optical Retarder/Compensator (BR) is caused to rotate about the Rotational Axis (RA) identified in FIGS. 1b, 2a and 3a, by the Physical Alignment System (AS) shown in FIG. 5a.

As this is done, at various effective Angles of Incidence of said Incident Electromagnetic Radiation Beam (LB), the Polarization State of said Incident Electromagnetic Radiation Beam (LB) and that of a Transmitted Electromagnetic Radiation Beam (LBT), (see FIGS. 5a, 6a and 6b), are monitored and Ratios of components of said two dimensional Jones Matrix are arrived from acquired data at by mathematical regression means. Ratios actually measured can be selected from the group consisting of:

Tpp/Tss;
Tps/Tpp;
Tsp/Tss;
Tps/Tss; and
Tsp/Tpp;

where (Tpp, Tss, Tps and Tsp) are components of a two-dimensional Jones Matrix:

$$\begin{bmatrix} Epo \\ Eso \end{bmatrix} = \begin{bmatrix} Tpp & Tsp \\ Tps & Tpp \end{bmatrix} \begin{bmatrix} Epi \\ Esi \end{bmatrix}$$

which describes the change in Polarization between an the Incident Electromagnetic Radiation Beam (LB) and a Transmitted Electromagnetic Radiation Beam (LBT) are calculated.

As described in the Disclosure of the Invention Section herein, the present invention method then provides that a Calibration Parameter containing Mathematical Model of a Berek-type Optical Retarder/Compensator be derived, said Calibration Parameter(s) comprising, typically, Indices of Refraction, a Thickness and Deviation Angle Calibration Parameters. Differences between indices of refraction where Off-Diagonal Ratios are found (eg. (Tps/Tpp), (Tps/Tss), (Tsp/Tpp) and (Tsp/Tss)); and Symmetry of a data about a Normal to an Alignment Surface where a Diagonal Ratio (Tss/Tpp) is found, are identifying of deviation of a Berek-type Retarder/Compensator Optical Axis from Perpendicular with respect to said Alignment Surface (AS) along orthogonal axes. Material System Mathematical Model regression onto a user selected Ratio Real, Imaginary or combined Real and Imaginary parts of one or more of said Ratios serve to provide numerical values for the Deviation Angle Calibration Parameters.

The method of the present invention can also include plotting of magnitude(s) of Ratios of Jones Matrix Components selected from the group consisting of: (Real, Imaginary, combination of Real and Imaginary), with respect to Angle of Incidence of an Electromagnetic Radiation Beam to an Alignment Surface of a Berek-type Optical Retarder/Compensator. Real parts of the Ratios are shown in FIGS. 8, 9 and 10.

FIG. 8 presents results obtained from investigation of Ideal Berek-type Optical Retarders/Compensators (BR) as demonstrated in FIGS. 1a–1d, over a range of Angles-of-Incidence taken both clockwise and counter-clockwise around an initial perpendicular orientation of an investigative Beam of Electromagnetic Radiation, with respect to said Alignment Surface (AS). Note that the plotted Real Part of the on-diagonal Ratio (Tpp/Tss) provides a center of symmetry of the data at an angle identified as zero (0.0) degrees. Said angle indicates coincidence of the Optical Axis (AO) with a perpendicular to the Alignment Surface (AS). Also plotted the Real Parts of off-diagonal Ratios (Tsp/Tss) and (Tps/Tpp) are seen to be essentially zero (0.0) over the range of utilized Angles-of-Incidence. (That is angles (phi) and (theta) in FIGS. 2a and 3a respectively are zero (0.0) degrees).

FIG. 9 presents results obtained from Non-Ideal Berek-type Optical Retarders/Compensators (BR) as demonstrated in FIGS. 3a–3d, over a range of Angles-of-Incidence taken both clockwise and counter-clockwise around an initial perpendicular orientation of an investigative Beam of Electromagnetic Radiation, with respect to said Alignment Surface (AS). Note that the plotted Real Part of on-diagonal Ratio (Tpp/Tss) provides a center of symmetry of the data at an angle identified as other than zero degrees, (ie. it is shifted approximately one-half (0.5) Degree along the "P" axis). Said other than zero angle indicates non-coincidence of the Optical Axis (AO) with a perpendicular to the Alignment Surface (AS). Also plotted are Real Parts of off-diagonal Ratios (Tsp/Tss) and (Tps/Tpp) are seen to be essentially zero (0.0) over the range of utilized Angles-of-Incidence. This indicates an offset of the Optical Axis with respect to a perpendicular to the Alignment Surface (A) in a direction effected by the non-zero value of the angle identified by (theta) in FIG. 3a.

FIG. 10 presents results obtained from Non-Ideal Berek-type Optical Retarders/Compensators (BR) as demonstrated in FIGS. 2a–2d over a range of Angles-of-Incidence taken both clockwise and counter-clockwise around an initial perpendicular orientation of an investigative Beam of Electromagnetic Radiation, with respect to said Alignment Surface (AS). Note that the plotted Real Part of on-diagonal Ratio (Tpp/Tss) provides a center of symmetry of the data at an angle identified as zero (0.0) degrees. Said angle indicates coincidence of the Optical Axis (AO) with a perpendicular to the Alignment Surface (AS). Also plotted are Real Parts of off-diagonal Ratios (Tsp/Tss) and (Tps/Tpp) are seen to be essentially non-zero over the range of utilized Angles-of-Incidence. This indicates that an investigative Beam of Electromagnetic Radiation was affected by more than one index of refraction as it passed through said Berek-type Optical Retarder/Compensator (BR). This indicates an offset of the Optical Axis with respect to a perpendicular to the Alignment Surface (A) in an "S" direction effected by the non-zero, (eg. approximately one-half (0.5) degree), value of the angle identified by (phi) in FIG. 2a.

(It is noted that similar results can be achieved by plotting of imaginary rather than real parts and by plotting combinations of real and imaginary parts of the identified ratios).

It should be appreciated that were a Berek-type Optical Retarder/Compensator with non-idealities as demonstrated in FIGS. 2a–2c and in FIGS. 3a–3c investigated, then a Plot of the Real Part of the magnitude of the ratio of (Tpp/Tss), with the point of symmetry shifted along the Angle of Incidence "X", axis away from the angle point Zero (0.0), (as shown in FIG. 8), and with the magnitudes of the real parts of the ratios Tps/Tpp, and Tsp/Tss not essentially Zero (0.0), (as shown in FIG. 9), would be obtained.

In any case, where an obtained plot of the real parts of the magnitudes of the relevant ratios differ from that shown in FIG. 8, a Berek-type Optical Retarder/Compensator under investigation is subject to being categorized as "Non-Qualified" because the Optical Axis (OA) is not oriented sufficiently perpendicular to a Alignment Surface (AS) thereof.

It is also noted that Berek-type (BR) and Non-Berek-type (NBR) Optical Retarders/Compensators differ primarily in how a Crystalline Material is cut. For instance, were the Diagram in FIG. 1b extended in the direction of the Optical Axis, and thinned in direction perpendicular thereto, and then trimmed to provide a circular cross-section as viewed from above, the Diagram in FIG. 4a would effectively result. It can then be appreciated why a "Tilting" of the Berek-type Optical Retarder/Compensator (BR) of FIG. 1b causes a similar action regarding the positioning of the Optical Axis (OA) therein, (with respect to "P" and "S" components of a Beam of Polarized Electromagnetic Radiation incident thereupon), as does "Rotating" the Non-Berek-type (NBR) Optical Retarder/Compensator (BR) of FIG. 4a. Because non-Berek-type Retarders/Compensators present an added difficulty in that both a Radial Direction of an Optical Axis and a deviation for Parallel to an Alignment Surface are unknown, the present invention method requires that a data set for evaluating representative ratios of components of a transmission Jones matrix be a function of both Angle-of-Incidence, (three (3) have been found sufficient), and Wavelength, (a multiplicity thereof are typically used), as compared to just Angle-of-Incidence where a Berek-type Retarder/Compensator is investigated. Where a Berek-type Retarder/Compensator is investigated it is known that the Optical Axis is generally in a locus approximately perpendicular to an Alignment Surface, hence there is no need to identify anything equivalent to an Optical Axis Radial Direction which presents in non-Berek-type Retarders/Compensators. (FIG. 4a demonstrated that a Radially Oriented Optical Axis Radial Direction in a non-Berek-type Retarder/Compensator can be directed anywhere in a range of from zero (0.0) to three-hundred-sixty (360) degrees). It is also noted that plots analogically similar to those shown in FIGS. 8, 9 and 10, but which would pertain to non-Berek-type Retarders/Compensators and would be plotted as a function of Wavelength, do not provide easily interpreted visual results. To practice the present invention with non-Berek-type Retarders/Compensators, based upon visual inspection of data plots, requires one obtain "Template" plots from known Ideal non-Berek-type Retarders/Compensators, as a function of Wavelength, and compare said "Template" plots to similar plots obtained from non-Berek-type Retarders/Compensators being evaluated for qualification. Sample plots for non-Berek-type Retarders/Compensators as a function of Wavelength, similar to those in FIGS. 8, 9, and 10 which are for Berek-type Retarders/Compensators as a function of Angle-of-Incidence, are not particularly instructive, and have not been provided herewith.

It is to be understood that this disclosure has, in conjunction with FIGS. 8, 9 and 10, demonstrated the identification of non-ideal orientation of an Optical Axis with respect to an Alignment Surface of a crystalline material, cut to provide a Berek-type Optical Retarder/Compensator, by separate identification of:

1. along a "P" plane Orthogonal Direction, displacement of Center of Symmetry of diagonal ratio (Tpp/Tss) data from zero degrees of "tilt", (as associated with an ideal Berek-type Optical Retarder/Compensator), as effected by differences in Indices of Refraction "seen" by "P" and "S" components of a Beam of Electromagnetic Radiation is caused to impinge upon said Alignment Surface of an Optical Retarder/Compensator at a multiplicity of "P" plane "tilts".

2. along a related "S" Orthogonal Direction, non-zero off-diagonal ratio (Tps/Tss) and (Tsp/Tss) magnitudes effected by differences in Indices of Refraction "seen" by "P" and "S" components of a Beam of Electromagnetic Radiation is caused to impinge upon said Alignment Surface of an Optical Retarder/Compensator along a locus oriented perpendicular to said Alignment Surface and at a multiplicity of "P" plane "tilts".

It is to be understood that the above approach to presentation, (utilizing "P" and "S" components in a Berek-type Optical Retarder/Compensator), was undertaken as it makes description of the present invention possible to present in a relatively understandable manner. However, the present invention can be practiced utilizing related Orthogonal Directions. Such an approach is, mathematically, simply an equivalent to what is described herein. Simple application of appropriate mathematical change of axis transform relationships can be produced to show the equivalence. It is therefore to be understood that while certain Claims recite a relatively easily understood embodiment of the present invention method utilizing "P" and "S" components, wherein the effects of Optical Axis deviation from ideal in "P" and "S" directions can be easily separated, (at least in Berek-type Retarders/Compensators), said Claims should be interpreted sufficiently broadly to include mathematical equivalents in which a mathematical change of related Orthogonal Axis transformation is utilized to, in a perhaps more difficult manner, accomplish the same end result. That is, for the purpose of Claim construction, the terms "P" and "S" are to be interpreted broadly enough to include use of mathematically equivalent orthogonal component sets. As well, terminology such as ellipsometer and ellipsometric and the like, is to be interprete sufficiently broad so as to include polarimeter systems.

It is further noted that reference to FIGS. 7c and 7d provide insight that a Trignometric relationship exists between Angle-of-Incidence of Polarized Beam of Electromagnetic Radiation (LB) with respect to a Material System (MAT) Alignment Surface (AS), and relative contribution indicies of refraction (IR1) and (IR3) to an index of refraction "seen" by a "P" or "S" component of said Polarized Beam of Electromagnetic Radiation (LB) as it passes through a Material System (MAT). FIG. 7e shows the Snell's Law effect of a change in Material System (MAT) refractive index, (n1 to n2), on a beam of electromagnetic radiation caused to be transmitted therethrough. (Note, the symbols θ1 and θ2 in FIG. 7e are distinct from the symbol θ as used in FIGS. 1a–1d, 2a–2c, 3a–3c and 4a–4d) Note as well, that a trigonometric relationship exists between the plane of the Alignment Surface (AS) of said Material System (MAT) and the direction of the Optical Axis (OA) with respect to said Alignment Surface (AS), as demonstrated in FIGS. 1a–1d, 2a–2c and 3a–3c. Said Trignometric relationships, in conjunction with Materials System (MAT) thickness, provide the basic elements of a mathematical model of a Material System (MAT). The present invention defines "Deviation Angle Calibration Parameters" as part of a mathematical model, which "Deviation Angle Calibration Parameters" identify alignment of an Optical Axis of a Material System with an Alignment Surface (AS) thereof, or a perpendicular to an Alignment Surface (AS) in non-Berek-type (NBR) and Berek-type (BR) Retarders/Compensators. Said "Deviation Angle Calibration Parameters" are what the present invention evaluates.

It is also to, be understood that an on-diagonal, (Tss/Tpp), ratio and off-diagonal ratios, ((Tps/Tpp), (Tps/Tss), (Tsp/Tpp) and (Tsp/Tss)), for an anisotropic material system are mathematically interrelated. That is, when one changes, changes necessarily occur in others. As well, such ratios are mathematically related to parameters typically associated with a materials system, such as the "PSI" and "DELTA" thereof. (See previously cited book by Azzam and Bashara for discussion of "PSI" and "DELTA" of a material system). In the Claims it is to be understood that where, for instance, an on-diagonal or off-diagonal ratio is specifically recited, a mathematical equivalent, such as for instance, a "PSI" or "DELTA", or combination thereof, parameter of the material system could be substituted therefor, and be within the scope of the Claims.

It is also to be understood that the foregoing Disclosure predominately utilized a "Crystalline Material" as a very relevant example of a material which presents with an Optical Axis. The Claims, however, use the terminology "Material System" to specifically indicate that the present invention can be applied to any material which presents with an Optical Axis, be it crystalline or not, and isotropic or anisotropic. It is to be understood that use of the present invention is therefore not limited to application only with Crystalline Materials.

The present invention is applicable both in aiding original manufacture of, and in the selection of, Material Systems such as Crystalline Optical Retarders/Compensators.

Finally, the present invention is not limited to application in any specific wavelength band. That is, any functional wavelength(s) of electromagnetic radiation can be utilized.

Having hereby disclosed the subject matter of the present invention, it should be obvious that many modifications, substitutions and variations of the present invention are possible in light of the teachings. It is therefore to be understood that the invention can be practiced other than as specifically described, and should be limited in breadth and scope only by the Claims.

I claim:

1. A method of qualifying a material system as having an optical axis oriented in a desired locus with respect to an alignment surface thereof, said method comprising, in a functional order, the steps of:

a. by ellipsometric techniques determining the magnitude (s) of at least one member of the group consisting of:
real, imaginary and a combination of real and imaginary components, for at least one ratio of components of a material system representing transmission Jones matrix as a function of at least one member of the group consisting of:
wavelength and "P" plane angle-of-incidence of an investigating polarized beam of electromagnetic radiation to an alignment surface of said material system and optical axis radial direction rotation angle, said at least one ratio of material system representing transmission Jones matrix components being selected from the group consisting of:
on-diagonal ratio
(Tpp/Tss);
and off-diagonal ratios
(Tsp/Tss);
(Tps/Tss);
(Tsp/Tpp);
(Tps/Tpp);

where Tpp, Tss, Tps and Tsp are the components of a two dimensional material system representing transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

which material system representing transmission Jones matrix describes the change in polarization state between said incident Epi and Esi and transmitted Epo and Eso portions of said beam of electromagnetic radiation;

b. providing a mathematical model of said material system comprising at least one deviation angle calibration parameter which represents a non-coincidence of said optical axis with a desired locus with respect to said alignment surface, said mathematical model serving to relate indices of refraction, thickness and optical axis direction over a range of at least one member of the group consisting of:

wavelength and "P" plane angles-of-incidence of an investigating polarized beam of electromagnetic radiation to an alignment surface of said material system and optical axis radial direction rotation angle;

c. performing a regression procedure of said mathematical model onto said magnitude of at least one member of the group consisting of:

real, imaginary and a combination of real and imaginary components, of at least one step a. selected ratio of material system representing transmission Jones matrix components as a function of at least one member of the group consisting of:

wavelength and "P" plane angle-of-incidence of an investigating polarized beam of electromagnetic radiation to an alignment surface of said material system and optical axis radial direction rotation angle, such that said at least one deviation angle calibration parameter is evaluated;

d. selecting acceptable range(s) of value(s) for said at least one direction deviation angle calibration parameter(s) and accepting as qualified a material system with value(s) for said at least one direction deviation angle calibration parameter(s), within said selected acceptable range(s).

2. A method of qualifying a material system as having an optical axis oriented in a desired locus with respect to an alignment surface thereof as in claim 1, said method further comprising the step of;

e. plotting magnitude(s) of at least one determined on-diagonal (Tpp/Tss) and/or off-diagonal ratio(s) selected from the group consisting of:

(Tps/Tpp) and (Tsp/Tss) and (Tps/Tss) and (Tsp/Tpp), with respect to at least one parameter selected from the group consisting of:

wavelength and "P" plane angle-of-incidence of said polarized beam of electromagnetic radiation to said alignment surface and optical axis radial direction rotation angle, and accepting said material system based upon observing said plot(s) only if said plot(s) essentially match known "template" plots.

3. A method of qualifying a material system as having an optical axis oriented in a desired locus with respect to an alignment surface thereof as in claim 1, which includes in step a. the alignment of said material system such that an incident beam of electromagnetic radiation caused to impinge upon a alignment surface thereof in a "P" plane effects an initial angle-of-incidence along a locus essentially normal to said alignment surface, and includes causing said incident beam of electromagnetic radiation to pass through a centrally located aperture in a quadrant detector, monitoring said portion of said incident beam of electromagnetic radiation is caused to reflect essentially perpendicularly back from said alignment surface with said quadrant detector, and adjusting said angle-of-incidence of said incident beam of electromagnetic radiation with respect to said alignment surface of said material system such that each quadrant of said quadrant detector detects an essentially equal magnitude of said reflected incident beam of electromagnetic radiation.

4. A method of qualifying a material system as having an optical axis oriented as desired with respect to an alignment surface thereof as in claim 1, in which the step b. determination of the complex magnitude of at least one material system representing transmission Jones matrix component ratio selected from the group consisting of:

on-diagonal ratio (Tpp/Tss) and off-diagonal ratios (Tps/Tpp), (Tsp/Tss), (Tps/Tss), (Tsp/Tpp);

comprises the steps of:

b1. setting the polarization state of said incident beam of electromagnetic radiation;

b2. monitoring the polarization state of said portion of said beam of electromagnetic radiation which is caused to be transmitted through said material system;

b3. selecting a plurality of combinations of the members of the group consisting of:

wavelength and "P" plane angle-of-incidence of an investigating polarized beam of electromagnetic radiation to an alignment surface of said material system and optical axis radial direction rotation angle, and repeating steps b1. and b2. for said plurality of combinations of the members of the group consisting of:

wavelength and "P" plane angle-of-incidence of an investigating polarized beam of electromagnetic radiation to an alignment surface of said material system and optical axis radial direction rotation angle;

b4. selecting monitored combinations of the members of the group consisting of:

wavelength and "P" plane angle-of-incidence of an investigating polarized beam of electromagnetic radiation to an alignment surface of said material system and optical axis radial direction rotation angle, and determining material system properties from polarization states of said set incident and monitored beam of electromagnetic radiation transmitted through said material system;

b5. repeating steps b1. through b4. utilizing different settings of polarization state in step b1. and mathematically determining, at said step b4. for monitored combinations of the members selected from the group consisting of:

wavelength and "P" plane angle-of-incidence of an investigating polarized beam of electromagnetic radiation to an alignment surface of said material system and optical axis radial direction rotation angle, the complex magnitude of at least one material system representing transmission Jones matrix component ratio selected from the group consisting of:

on-diagonal ratio (Tpp/Tss) and off-diagonal ratios (Tps/Tpp), (Tsp/Tss), (Tps/Tss), (Tsp/Tpp).

5. A method of qualifying a material system as having an optical axis oriented perpendicular to an alignment surface thereof, said method comprising, in a functional order, the steps of:

a. selecting a wavelength of electromagnetic radiation and aligning a material system such that an incident polarized beam of electromagnetic radiation of said selected wavelength is caused to impinge upon an alignment surface of said material system with an angle-ofincidence in a "P" plane, and such that a portion of said beam of electromagnetic radiation is caused to be transmitted through said material system;

b. selecting a plurality of "P" plane angles-of-incidence of said incident polarized beam of electromagnetic radiation with respect to said alignment surface and for said plurality of "P" plane angles-of-incidence, determining by ellipsometric techniques:

the complex magnitude of at least one material system representing transmission Jones matrix component ratio selected from the group consisting of:
on-diagonal ratio
(Tpp/Tss)
and off-diagonal ratios
(Tps/Tpp);
(Tsp/Tss);
(Tps/Tss);
(Tsp/Tpp);

where Tpp, Tss, Tps and Tsp are the components of a two dimensional material system representing transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

which material system representing transmission Jones matrix describes the change in polarization state between said incident Epi and Esi and transmitted Epo and Eso portions of said beam of electromagnetic radiation;

c. providing a mathematical model for said material system comprising "P" and "S" direction deviation angle calibration parameters, said mathematical model serving to relate material system indices of refraction, thickness and optical axis direction orientation at a plurality of wavelengths and incident polarized beam of electromagnetic radiation angles-of-incidence with respect to said alignment surface; appropriate values of which "P" and "S" direction deviation angle calibration parameters serve to make said model internally consistent with respect to:

the complex magnitude of said at least one material system representing transmission Jones matrix component ratio selected from the group consisting of:
on-diagonal ratio (Tpp/Tss), and off-diagonal ratios, (Tps/Tpp), (Tsp/Tss), (Tps/Tss), (Tsp/Tpp);

d. performing a mathematical regression of the mathematical model onto:

the magnitude of at least one component selected from the group consisting of:
the real part, the imaginary part and a combination of real and imaginary parts, of said at least one material system representing transmission Jones matrix component ratio selected from the group consisting of:
on-diagonal ratio (Tpp/Tss), and off-diagonal ratios (Tps/Tpp), (Tsp/Tss), (Tps/Tss), (Tsp/Tpp), as a function of "P" plane angle-of-incidence of said beam of electromagnetic radiation with respect to said alignment surface, the purpose of said mathematical regression being to determine reduced square error numerical values for said "P" and "S" direction deviation angle calibration parameters, said "P" and "S" direction deviation calibration parameters being angular offsets of said optical axis from an ideal perpendicular orientation to said alignment surface in said "P" and "S" orthogonal directions respectively; and e. selecting an acceptable range of values for each of said "P" and "S" direction deviation angle calibration parameters and accepting as qualified a material system with values for said "P" and "S" direction deviation angle calibration parameters, within said selected acceptable ranges.

6. A method of qualifying a material system as having an optical axis oriented perpendicular to an alignment surface thereof as in claim 5, said method further comprising at least one step selected from the following steps f. and g.:

f. plotting magnitude(s) of at least one of said ratio(s) determined in step b. with respect to angle-of-incidence of said polarized beam of electromagnetic radiation to said alignment surface and accepting said material system based upon observing said plots only if a plot for an on-diagonal ratio (Tss/Tpp) is symmetrical around an angle-of-incidence of said polarized beam of electromagnetic radiation to said alignment surface which results when said polarized beam of electromagnetic radiation is essentially coincident with a normal to said alignment surface, and determined off-diagonal ((Tps/Tpp) and (Tsp/Tss) and (Tps/Tss) and (Tsp/Tpp)), ratio(s) are essentially zero (0.0) over the entire range of said angles-of-incidence of said polarized beam of electromagnetic radiation to said alignment surface;

g. plotting magnitude(s) of at least one determined on-diagonal (Tpp/Tss) and/or off-diagonal ratio(s) selected from the group consisting of:
(Tps/Tpp) and (Tsp/Tss) and (Tps/Tss) and (Tsp/Tpp), with respect to angle-of-incidence of said polarized beam of electromagnetic radiation to said alignment surface, and accepting said material system based upon observing said plot(s) only if said plot(s) essentially match known "template" plots over the entire range of said angles-of-incidence of said polarized beam of electromagnetic radiation to said alignment surface.

7. A method of qualifying a material system as having an optical axis oriented perpendicular to an alignment surface thereof as in claim 5, which includes in step a. the alignment of a material system such that an incident beam of electromagnetic radiation caused to impinge upon a alignment surface thereof in a "P" plane effects an initial angle-of-incidence along a locus essentially normal to said alignment surface, and includes causing said incident beam of electromagnetic radiation to pass through a centrally located aperture in a quadrant detector, monitoring said portion of said incident beam of electromagnetic radiation is caused to reflect essentially perpendicularly back from said alignment surface with said quadrant detector, and adjusting said angle-of-incidence of said incident beam of electromagnetic radiation with respect to said alignment surface of said material system such that each quadrant of said quadrant detector detects an essentially equal magnitude of said reflected incident beam of electromagnetic radiation.

8. A method of qualifying a material system having an optical axis oriented perpendicular to an alignment surface thereof as in claim 5, in which the step b. determination of the complex magnitude of at least one material system representing transmission Jones matrix component ratio selected from the group consisting of:
on-diagonal ratio (Tpp/Tss) and off-diagonal ratios (Tps/Tpp), (Tsp/Tss), (Tps/Tss), (Tsp/Tpp);
comprises the steps of:

b1. setting the polarization state of said incident beam of electromagnetic radiation;

b2. monitoring the polarization state of said portion of said beam of electromagnetic radiation which is caused to be transmitted through said material system;

b3. selecting a plurality of "P" plane angles-of-incidence of said incident polarized beam of electromagnetic radiation with respect to said alignment surface and repeating steps b1. and b2. for said plurality of "P" plane angles-of-incidence;

b4. selecting monitored "P" plane angles-of-incidence and at said selected "P" plane angles-of-incidence, determining material system properties from polarization states of said set incident and monitored beam of electromagnetic radiation transmitted through said material system;

b5. repeating steps b1. through b4. utilizing different settings of polarization state in step b1. and mathematically determining, at said step b4. selected monitored "P" plane angles-of-incidence, the complex magnitude of at least one material system representing transmission Jones matrix component ratio selected from the group consisting of:
on-diagonal ratio (Tpp/Tss) and off-diagonal ratios (Tps/Tpp), (Tsp/Tss), (Tps/Tss), (Tsp/Tpp).

9. A method of qualifying a material system as having an optical axis oriented radially in, and parallel to an alignment surface thereof, said method comprising, in a functional order, the steps of:

a. aligning a material system such that an incident polarized beam of electromagnetic radiation is caused to impinge upon an alignment surface of said material system with an angle-of-incidence in a "P" plane, and such that a portion of said beam of electromagnetic radiation is caused to be transmitted through said material system;

b. selecting a plurality of wavelengths and selecting a plurality of "P" plane angles-of-incidence of said incident polarized beam of electromagnetic radiation with respect to said alignment surface and for said plurality of wavelengths and plurality of "P" plane angles-of-incidence, determining by ellipsometric techniques:
the complex magnitude of at least one material system representing transmission Jones matrix component ratio selected from the group consisting of:
on-diagonal ratio
(Tpp/Tss);
and off-diagonal ratios
(Tps/Tpp);
(Tsp/Tss);
(Tps/Tss);
(Tsp/Tpp);

where Tpp, Tss, Tps and Tsp are the components of a two dimensional materials system representing transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

which materials system representing transmission Jones matrix describes the change in polarization state between said incident Epi and Esi and transmitted Epo and Eso portions of said beam of electromagnetic radiation;

c. providing a mathematical model for said material system comprising "radial angular direction location" and "deviation from parallel to alignment surface plane deviation angle" calibration parameters, said mathematical model serving to relate material system indices of refraction, thickness and optical axis orientation at a plurality of wavelengths and incident polarized beam of electromagnetic radiation angles-of-incidence, appropriate values of which "radial angular direction location" and "deviation from parallel to alignment surface plane deviation angle" calibration parameters serve to make said model internally consistent with respect to:
the complex magnitude of said at least one materials system representing transmission Jones matrix component ratio selected from the group consisting of:
on-diagonal ratio (Tpp/Tss) and off-diagonal ratios (Tps/Tpp), (Tsp/Tss), (Tps/Tss), (Tsp/Tpp);

d. performing a mathematical regression of the mathematical model onto:
the magnitude of at least one component selected from the group consisting of:
the real part, the imaginary part and a combination of real and imaginary parts, of said at least one material system representing transmission Jones matrix component ratio selected from the group consisting of:
on-diagonal ratio (Tpp/Tss) and off-diagonal ratios (Tps/Tpp), (Tsp/Tss), (Tps/Tss) (Tsp/Tpp), as a function of wavelength and of "P" plane angle-of-incidence of said polarized beam of electromagnetic radiation with respect to said alignment surface, the purpose of said mathematical regression being to determine reduced square error numerical values for said "radial angular direction location" and "deviation from parallel to alignment surface plane deviation angle" calibration parameters, said "deviation from parallel to alignment surface plane deviation angle" calibration parameter being an angular offset of said optical axis from an ideal parallel orientation to said alignment surface; and e. selecting an acceptable range of values for said "deviation from parallel to alignment surface plane deviation angle" and accepting as qualified a material system with a value for said "deviation from parallel to alignment surface plane deviation angle" calibration parameter, within said selected acceptable range.

10. A method of qualifying a material system as having an optical axis oriented radially in, and parallel to an alignment surface thereof as in claim 9, which further comprises the step of:

f. plotting magnitude(s) of at least one determined on-diagonal (Tpp/Tss) and/or off-diagonal ratio(s) selected from the group consisting of:
(Tps/Tpp) and (Tsp/Tss) and (Tps/Tss) and (Tsp/Tpp), with respect to wavelength at at least one angle-of-incidence of said polarized beam of electromagnetic radiation to said alignment surface, and accepting said material system based upon observing said plot(s) only if said plot(s) essentially match known "template" plot(s) over the entire range of said wavelengths of said polarized beam of electromagnetic radiation to said alignment surface.

11. A method of qualifying a material system as having an optical axis oriented radially from a central point and parallel to an alignment surface thereof as in claim 9, which includes in step a. the alignment of a material system such that an incident beam of electromagnetic radiation caused to impinge upon a alignment surface thereof in a "P" plane effects an initial angle-of-incidence along a locus essentially normal to said alignment surface, and includes causing said incident beam of electromagnetic radiation to pass through a centrally located aperture in a quadrant detector, monitoring said portion of said incident beam of electromagnetic radiation is caused to reflect essentially perpendicularly back from said alignment surface with said quadrant detector, and adjusting said angle-of-incidence of said incident beam of electromagnetic radiation with respect to said alignment surface of said material system such that each quadrant of said quadrant detector detects an essentially equal magnitude of said reflected incident beam of electromagnetic radiation.

12. A method of qualifying a material system as having an optical axis oriented radially in, and parallel to an alignment surface thereof as in claim 9, in which the step b. determination of the complex magnitude of at least one material system representing transmission Jones matrix component ratio selected from the group consisting of:

on-diagonal ratio (Tpp/Tss) and off-diagonal ratios (Tps/Tpp), (Tsp/Tss), (Tps/Tss), (Tsp/Tpp), comprises the steps of:

b1. setting the polarization state of said incident beam of electromagnetic radiation;

b2. monitoring the polarization state of said portion of said beam of electromagnetic radiation which is caused to be transmitted through said material system;

b3. selecting a plurality of wavelengths and "P" plane angles-of-incidence of said incident polarized beam of electromagnetic radiation with respect to said alignment surface and repeating steps b1. and b2. for said plurality of wavelengths and "P" plane angles-of-incidence;

b4. selecting monitored wavelengths and "P" plane angles-of-incidence and at said selected wavelength and "P" plane angles-of-incidence, determining material system properties from polarization states of said set incident and monitored beam of electromagnetic radiation transmitted through said material system;

b5. repeating steps b1. through b4. utilizing different settings of polarization state in step b1. and mathematically determining, at said step b4. selected monitored wavelengths and "P" plane angles-of-incidence, the complex magnitude of at least one material system representing transmission Jones matrix component ratio selected from the group consisting of:

on-diagonal ratio (Tpp/Tss) and off-diagonal ratios (Tps/Tpp), (Tsp/Tss), (Tps/Tss), (Tsp/Tpp).

13. A method of qualifying a material system as having an optical axis oriented radially in, and parallel to an alignment surface thereof, said method comprising, in a functional order, the steps of:

a. aligning a material system such that an incident polarized beam of electromagnetic radiation is caused to impinge upon an alignment surface of said material system with an angle-of-incidence in a "P" plane, and such that a portion of said beam of electromagnetic radiation is caused to be transmitted through said material system;

b. selecting a plurality of optical axis radial direction rotation angles and selecting a plurality of "P" plane angles-of-incidence of said incident polarized beam of electromagnetic radiation with respect to said alignment surface and for said plurality of optical axis radial direction rotation angles and plurality of "P" plane angles-of-incidence, determining by ellipsometric techniques:

the complex magnitude of at least one material system representing transmission Jones matrix component ratio selected from the group consisting of:

on-diagonal ratio
(Tpp/Tss)
and off-diagonal ratios
(Tps/Tpp);
(Tsp/Tss);
(Tps/Tss);
(Tsp/Tpp);

where Tpp, Tss, Tps and Tsp are the components of a two dimensional material system representing transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

which material system representing transmission Jones matrix describes the change in polarization state between said incident Epi and Esi and transmitted Epo and Eso portions of said beam of electromagnetic radiation;

c. providing a mathematical model for said material system comprising "radial angular direction location" and "deviation from parallel to alignment surface plane deviation angle" calibration parameters, said mathematical model serving to relate material system indices of refraction, thickness and optical axis orientation at a plurality of optical axis radial direction rotation angles and incident polarized beam of electromagnetic radiation angles-of-incidence with respect to said alignment surface, appropriate values of which "radial angular direction location" and "deviation from parallel to alignment surface plane deviation angle" calibration parameters serve to make said model internally consistent with respect to:

the complex magnitude of said at least one material system representing transmission Jones matrix component ratio selected from the group consisting of:

on-diagonal ratio (Tpp/Tss) and off-diagonal ratios (Tps/Tpp), (Tsp/Tss), (Tps/Tss), (Tsp/Tpp);

d. performing a mathematical regression of the mathematical model onto:

the magnitude of at least one component selected from the group consisting of:

the real part, the imaginary part and a combination of real and imaginary parts, of said at least one material system representing transmission Jones matrix component ratio selected from the group consisting of:

on-diagonal ratio (Tpp/Tss) and off-diagonal ratios (Tps/Tpp), (Tsp/Tss), (Tps/Tss), (Tsp/Tpp), as a function of optical axis radial direction rotation angle and of "P" plane angle-of-incidence of said polarized beam of electromagnetic radiation with respect to said alignment surface, the purpose of said mathematical regression being to determine reduced square error numerical values for said "radial angular direction location" and "deviation from parallel to alignment surface plane deviation angle" calibration parameters, said "deviation from parallel to alignment surface plane deviation angle" calibration parameter being an angular offset of said optical axis from an ideal parallel orientation to said alignment surface; and e. selecting an acceptable range of values for said "deviation from parallel to alignment surface plane deviation angle" and accepting as qualified a material system with a value for said "deviation from parallel to alignment surface plane deviation angle" calibration parameter, within said selected acceptable range.

14. A method of qualifying a material system as having an optical axis oriented radially in, and parallel to an alignment surface thereof as in claim 13, which further comprises the step of:
   f. plotting magnitude(s) of at least one determined on-diagonal (Tpp/Tss) and/or off-diagonal ratio(s) selected from the group consisting of:
      (Tps/Tpp) and (Tsp/Tss) and (Tps/Tss) and (Tsp/Tpp), with respect to optical axis radial direction rotation angles at at least one angle-of-incidence of said polarized beam of electromagnetic radiation to said alignment surface, and accepting said material system based upon observing said plot(s) only if said plot(s) essentially match known "template" plot(s) over the entire range of said optical axis radial direction rotation angles.

15. A method of qualifying a material system as having an optical axis oriented radially from a central point and parallel to an alignment surface thereof as in claim 13, which includes in step a. the alignment of a material system such that an incident beam of electromagnetic radiation caused to impinge upon a alignment surface thereof in a "P" plane effects an initial angle-of-incidence along a locus essentially normal to said alignment surface, and includes causing said incident beam of electromagnetic radiation to pass through a centrally located aperture in a quadrant detector, monitoring said portion of said incident beam of electromagnetic radiation is caused to reflect essentially perpendicularly back from said alignment surface with said quadrant detector, and adjusting said angle-of-incidence of said incident beam of electromagnetic radiation with respect to said alignment surface of said material system such that each quadrant of said quadrant detector detects an essentially equal magnitude of said reflected incident beam of electromagnetic radiation.

16. A method of qualifying a material system as having an optical axis oriented radially in, and parallel to an alignment surface thereof as in claim 13, in which the step b. determination of the complex magnitude of at least one materials system representing transmission Jones matrix component ratio selected from the group consisting of:
   on-diagonal ratio (Tpp/Tss) and off-diagonal ratios (Tps/Tpp), (Tsp/Tss), (Tps/Tss), (Tsp/Tpp),
   comprises the steps of:
   b1. setting the polarization state of said incident beam of electromagnetic radiation;
   b2. monitoring the polarization state of said portion of said beam of electromagnetic radiation which is caused to be transmitted through said material system;
   b3. selecting a plurality of optical axis radial direction rotation angle and "P" plane angles-of-incidence of said incident polarized beam of electromagnetic radiation with respect to said alignment surface and repeating steps b1. and b2. for said plurality of wavelengths and "P" plane angles-of-incidence;
   b4. selecting monitored optical axis radial direction rotation angles and "P" plane angles-of-incidence and at said selected optical axis radial direction rotation angles and "P" plane angles-of-incidence, determining material system properties from polarization states of said set incident and monitored beam of electromagnetic radiation transmitted through said material system;
   b5. repeating steps b1. through b4. utilizing different settings of polarization state in step b1. and mathematically determining, at said step b4. selected monitored optical axis radial direction rotation angles and "P" plane angles-of-incidence, the complex magnitude of at least one material system representing transmission Jones matrix component ratio selected from the group consisting of:
      on-diagonal ratio (Tpp/Tss) and off-diagonal ratios (Tps/Tpp), (Tsp/Tss), (Tps/Tss), (Tsp/Tpp).

17. A method of qualifying a material system as having an optical axis oriented in a desired locus with respect to an alignment surface thereof, said method comprising, in a functional order, the steps of:
   a. by ellipsometric techniques determining the magnitude(s) of at least one member of the group consisting of:
      real, imaginary and a combination of real and imaginary components, for at least one ratio of components of a material system representing transmission Jones matrix as a function of at least one member of the group consisting of:
         wavelength and "P" plane angle-of-incidence of an investigating polarized beam of electromagnetic radiation to an alignment surface of said material system and optical axis radial direction rotation angle, said at least one ratio of material system representing transmission Jones Matrix components being selected from the group consisting of:
         on-diagonal ratio
            (Tpp/Tss);
         and off-diagonal ratios
            (Tsp/Tss);
            (Tps/Tss);
            (Tsp/Tpp);
            (Tps/Tpp);
   where Tpp, Tss, Tps and Tsp are the components of a two dimensional material system representing transmission Jones matrix:

$$\begin{bmatrix} Epo \\ Eso \end{bmatrix} = \begin{bmatrix} Tpp & Tsp \\ Tps & Tss \end{bmatrix} \begin{bmatrix} Epi \\ Esi \end{bmatrix}$$

which material system representing transmission Jones matrix describes the change in polarization state between said incident Epi and Esi and transmitted Epo and Eso portions of said beam of electromagnetic radiation;
   b. plotting magnitude(s) of at least one determined on-diagonal (Tpp/Tss) and/or off-diagonal ratio(s) selected from the group consisting of:
      (Tps/Tpp) and (Tsp/Tss) and (Tps/Tss) and (Tsp/Tpp), with respect to at least one parameter selected from the group consisting of:
         wavelength and "P" plane angle-of-incidence of said polarized beam of electromagnetic radiation to said alignment surface and optical axis radial direction rotation angle, and accepting said material system based upon observing said plot(s) only if said plot(s) essentially match known "template" plot(s) over the entire range of said at least one parameter selected from the group consisting of:
         wavelength and "P" plane angle-of-incidence of said polarized beam of electromagnetic radiation to said alignment surface and optical axis radial direction rotation angle.

* * * * *